US011112379B2

(12) United States Patent
Shalev et al.

(10) Patent No.: US 11,112,379 B2
(45) Date of Patent: *Sep. 7, 2021

(54) MOLECULAR SENSOR BASED ON VIRTUAL BURIED NANOWIRE

(71) Applicant: Ramot at Tel-Aviv University Ltd., Tel-Aviv (IL)

(72) Inventors: Gil Shalev, Ramat-HaSharon (IL); Yossi Rosenwaks, Hod-HaSharon (IL)

(73) Assignee: Ramot at Tel-Aviv University Ltd., Tel-Aviv (IL)

(*) Notice: Subject to any disclaimer, the term of this patent is extended or adjusted under 35 U.S.C. 154(b) by 554 days.

This patent is subject to a terminal disclaimer.

(21) Appl. No.: 16/027,403

(22) Filed: Jul. 5, 2018

(65) Prior Publication Data

US 2018/0328882 A1 Nov. 15, 2018

Related U.S. Application Data

(63) Continuation of application No. 14/380,732, filed as application No. PCT/IL2013/050182 on Feb. 28, 2013, now Pat. No. 10,054,562.

(Continued)

(51) Int. Cl.
*G01N 33/551* (2006.01)
*G01N 27/414* (2006.01)
(Continued)

(52) U.S. Cl.
CPC ......... *G01N 27/4145* (2013.01); *G01N 27/12* (2013.01); *G01N 27/30* (2013.01);
(Continued)

(58) Field of Classification Search
CPC .... G01N 27/4145; G01N 27/12; G01N 27/30; G01N 27/4146; G01N 33/551; G01N 33/54373; H01L 21/22; H01L 21/324
(Continued)

(56) References Cited

U.S. PATENT DOCUMENTS 5,021,999 A 6/1991 Kohda et al.
5,214,303 A 5/1993 Aoki
(Continued)

FOREIGN PATENT DOCUMENTS

WO WO 2013/128456 9/2013
WO WO 2013/156990 10/2013

OTHER PUBLICATIONS

"Silicon Nanowire on Oxide/Nitride/Oxide for Memory Application", Nanotechnology,18(23):1-4, May 16, 2007.
(Continued)

*Primary Examiner* — Christopher L Chin

(57) ABSTRACT

The present invention provides a method and a system based on a multi-gate field effect transistor for sensing molecules in a gas or liquid sample. The said FET transistor comprises dual gate lateral electrodes (and optionally a back gate electrode) located on the two sides of an active region, and a sensing surface on top of the said active region. Appling voltages to the lateral gate electrodes, creates a conductive channel in the active region, wherein the width and the lateral position of the said channel can be controlled. Enhanced sensing sensitivity is achieved by measuring the channels conductivity at a plurality of positions in the lateral direction. The use of an array of the said FTE for electronic nose is also disclosed.

18 Claims, 12 Drawing Sheets

Related U.S. Application Data

(60) Provisional application No. 61/604,041, filed on Feb. 28, 2012.

(51) Int. Cl.

| | |
|---|---|
| *G01N 33/543* | (2006.01) |
| *G01N 27/12* | (2006.01) |
| *G01N 27/30* | (2006.01) |
| *H01L 21/22* | (2006.01) |
| *H01L 21/324* | (2006.01) |

(52) U.S. Cl.
CPC ... *G01N 27/4146* (2013.01); *G01N 33/54373* (2013.01); *H01L 21/22* (2013.01); *H01L 21/324* (2013.01); *G01N 33/551* (2013.01)

(58) Field of Classification Search
USPC ............... 422/82.01; 436/524, 525, 527, 806
See application file for complete search history.

(56) References Cited

U.S. PATENT DOCUMENTS

| | | | |
|---|---|---|---|
| 5,414,693 A | 5/1995 | Ma et al. | |
| 5,434,825 A | 7/1995 | Harari | |
| 6,943,404 B2 | 9/2005 | Huang et al. | |
| 7,402,862 B2 | 7/2008 | Choi et al. | |
| 7,405,969 B2 | 7/2008 | Eitan | |
| 8,007,727 B2 | 8/2011 | Shalev et al. | |
| 8,241,913 B2 | 8/2012 | Shalev et al. | |
| 8,318,505 B2 | 11/2012 | Shalev et al. | |
| 8,542,517 B2 * | 9/2013 | Li | G11C 17/18 365/104 |
| 10,054,562 B2 * | 8/2018 | Shalev | H01L 21/22 |
| 2010/0198521 A1 | 8/2010 | Haick et al. | |
| 2011/0304317 A1 | 12/2011 | Shalev et al. | |
| 2015/0017740 A1 | 1/2015 | Shalev et al. | |

OTHER PUBLICATIONS

Communication Pursuant to Article 94(3) EPC dated Dec. 19, 2017 From the European Patent Office Re. Application No. 13754335.1. (4 Pages).
International Preliminary Report on Patentability dated Sep. 12, 2014 From the International Bureau of WIPO Re. Application No. PCT/IL2013/050182.
International Preliminary Report on Patentability dated Oct. 30, 2014 From the International Bureau of WIPO Re. Application No. PCT/ IL2013/050244.
International Search Report and the Written Opinion dated Jun. 13, 2013 From the International Searching Authority Re. Application No. PCT/ IL2013/050244.
International Search Report and the Written Opinion dated May 29, 2013 From the International Searching Authority Re. Application No. PCT/ IL2013/050182.
Office Action dated Aug. 17, 2015 From The Patent Office of the State Intellectual Property Office of the People's Republic of China Re. Application No. 201380013517.8 and Its Translation Into English.
Official Action dated Jan. 16, 2018 From the US Patent and Trademark Office Re. U.S. Appl. No. 14/380,732. (13 pages).
Restriction Official Action dated Aug. 24, 2017 From the US Patent and Trademark Office Re. U.S. Appl. No. 14/380,732. (9 pages).
Supplementary European Search Report and the European Search Opinion dated Sep. 30, 2015 From the European Patent Office Re. Application No. 13754335.1.
Ahn et al. "Double-Gate Nanowire Field Effect Transistior for a Biosensor", Nano Letter, XP055163613, 10(8): 2934-2938, Jul. 12, 2010. Abstract, Figs.1, 2, 4, p. 2935-2936.
Ahn et al. "Investigation of Size Dependence on Sensitivity for Nanowire FET Biosensors", IEEE Transactions on Nanotechnology, 10(6): 1405-1411, May 27, 2011. p. 1405-1411.
Chan et al. "A True Single-Transistor Oxide-Nitride-Oxide EEPROM Device", IEEE Electron Device Letters, EDL-8(3): 93-95, Mar. 1987.
Fu et al. "Si-Nanowire Based Gate-All-Around Nonvolatile SONOS Memory Cell", IEEE Electron Device Letters, 29(5): 518-521, May 2008.
Haick et al. "Electrical Characteristics and Chemical Stability of Non-Oxidized, Methyl-Terminated Silicon Nanowires", Journal of the American Chemical Society, 128(28): 8990-8991, Jun. 27, 2006. p. 8990-8991.
Kapetanakis et al. "Charge Storage and Interface States Effects in Si-Nanocrystal Memory Obtained Using Low-Energy Si+ Implantation and Annealing", Applied Physics Letters, 77(21): 3450-3452, Nov. 20, 2000.
Lee et al. "A Novel Self-Aligned 4-Bit SONOS-Type Nonvolatile Memory Cell With T-Gate and I-Shape FinFET Structure", IEEE Trabsactions on Electron Devices, 57(8): 1728-1736, Aug. 2010. Abstract, Fig. 1n.
Lee et al. "Layer-by-Layer Assembled Charge-Trap Memory Devices With Adjustable Electronic Properties", Nanotechnology, 3: 790-795. Dec. 2007.
Li et al. "Silicon Nanowire on Oxide/Nitride/Oxide for Memory Application", Nanotechnology, 18(23): 235204-1-235204-4, May 16, 2007.
Lin et al. "Read Characteristics of Independant Double-Gate Poly-Si Nanowire SONOS Devices", IEEE Transactions on Electron Devices, 58(11): 3771-3777, Nov. 11, 2011.
Shalev et al. "Specific and Label-Free Femtomolar Biomarker Detection With an Electrostatically Formed Nanowire Biosensor", NPG Asia Materials, 5(E41): 1-7, Mar. 1, 2013.
Sun et al. "Vertical-Si-Nanowire-Based Nonvolatile Memory Devices With Improved Performance and Reduced Process Complexity", IEEE Transactions on Electron Devices, 58(5): 1329-1335, May 2011.
Tiwari et al. "A Silicon Nanocrystals Based Memory", Applied Physics Letters, 68(10): 1377-1379, Mar. 4, 1996.
Young et al. "Charge Transport and Trapping Characteristics in Thin Nitride-Oxide Stacked Films", IEEE Electron Device Letters, 9(11): 616-618, Nov. 1988.

* cited by examiner

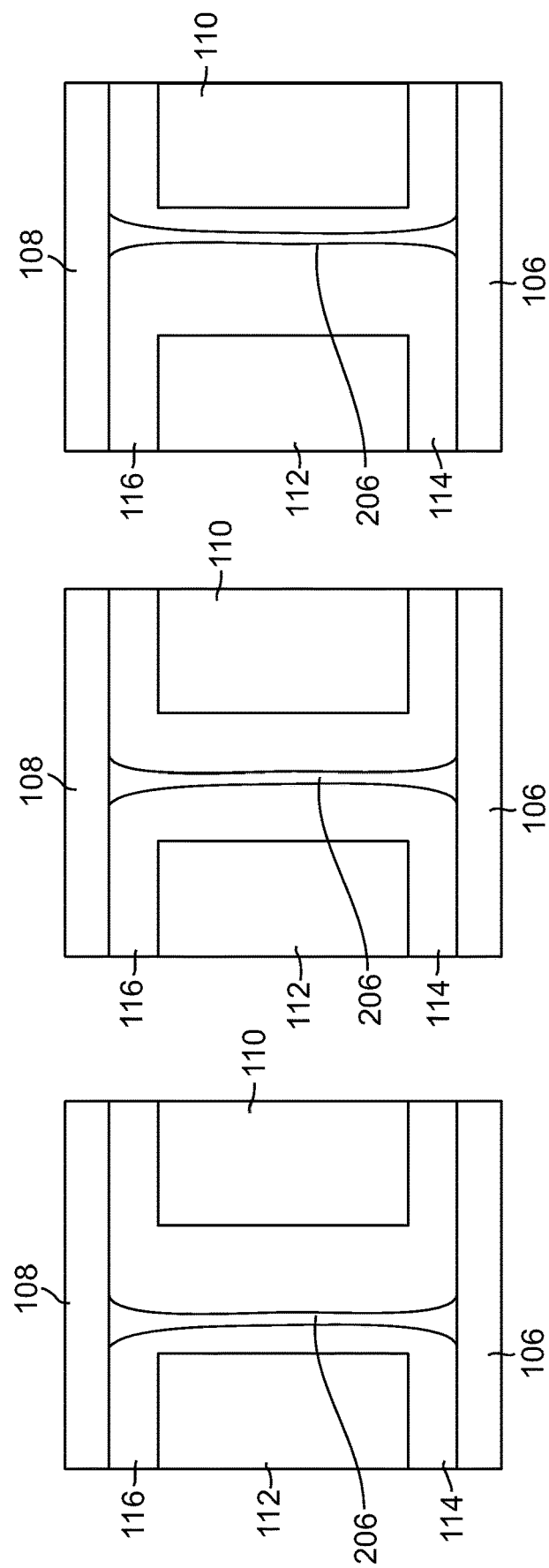

MOLECULAR SENSOR BASED ON VIRTUAL BURIED NANOWIRE

RELATED APPLICATIONS

This application is a continuation of U.S. patent application Ser. No. 14/380,732 filed on Aug. 25, 2014, which is a National Phase of PCT Patent Application No. PCT/IL2013/050182 having International Filing Date of Feb. 28, 2013, which claims the benefit of priority under 35 U.S.C. § 119(e) from U.S. Provisional Patent Application No. 61/604,041 filed on Feb. 28, 2012. The contents of the above applications are all incorporated by reference as if fully set forth herein in their entirety.

FIELD AND BACKGROUND OF THE INVENTION

The present invention, in some embodiments thereof, relates to a semiconductor chemical sensor and, more particularly, but not exclusively, to a gas sensor based on a field effect transistor.

Commercially available gas sensors include IR sensors, Toxic sensors, and Pellistors, all sold by City Technology, Ltd., and metal oxide gas detectors, sold by Figaro USA, Inc. (FIS, Inc.). The sensors sold by City Technology are described, for example, at worldwideweb(dot)citytech(dot)com, and the sensors sold by Figaro are described, for example, at worldwideweb(dot)figarosensor(dot)com. Gas sensors that could be manufactured more cheaply, and/or have greater sensitivity and/or greater specificity, would be useful.

Gas sensors based on nanowire of various materials, for example Si, ZnO, SnO, and other materials, can exhibit exceptionally high resolution and sensitivity. However, the manufacture of commercial gas sensors based on such nanowires may not be feasible at the present time, since the fabrication of these structures, for example with the VLS method, cannot accommodate high volume manufacturing (HVM). Alternatively, high volume CMOS manufacturing of nanowires could be realized in the future but with a substantial increase in cost, even several orders of magnitude.

Additional background art includes U.S. Pat. No. 6,173,602 to Moseley, "Transition metal oxide gas sensor;" WO 2005/004204 to Heath, "An electrochemical method and resulting structures for attaching molecular and biomolecular structures to semiconductor micro and nanostructures;" WO 2008/030395 to Amori, "Apparatus and method for quantitative determination of target molecules;" WO 2009/013754 to Haick, "Chemically sensitive field effect transistors and uses thereof in electronic nose devices;" U.S. Pat. No. 7,628,959 to Penner, "Hydrogen gas sensor;" U.S. Pat. No. 7,631,540 to Chueh, "Gas sensors with zinc oxide or indium/zinc mixed oxides and method of detecting NOX gas;" U.S. Pat. No. 7,662,652 to Zhou, "Chemical sensor using semiconducting metal oxide nanowires;" US 2010/0198521 to Haick, "Chemically sensitive field effect transistors and uses thereof in electronic noise devices;" U.S. Pat. No. 7,963,148 to Liu, "Gas sensor made of field effect transistor made of ZnO nanowires;" Zhou et al, "Silicon Nanowires as Chemical Sensors," Chem. Phys. Lett. 369 p.220 (2003); Eliol et al, "Integrated Nanoscale Silicon Sensors Using Top-Down Fabrication," Appl. Phys. Lett. 83 p.4613 (2003); Sysoev et al, "Toward the nanoscopic 'electronic nose': hydrogen vs. carbon monoxide discrimination with an array of individual metal oxide nano- and mesowire sensors," Nano Lett. 6(8):1584-8 (2006); McAlpine et al, "Highly ordered nanowire arrays on plastic substrates for ultrasensitive flexible chemical sensors," Nature mater. 6(5) 379-384 (2007); Sysoev et al, "A Gradient Microarray Electronic Nose Based on Percolating SnO2 Nanowire Sensing Elements," NANO LETTERS, Vol. 7, No. 10, 3182-3188; McAlpine et al, "Peptide-Nanowire Hybrid Materials for Selective Sensing of Small Molecules," Peptide-Nanowire Hybrid Materials for Selective Sensing of Small Molecules (2008); Engel et al, "Supersensitive Detection of Explosives by Silicon Nanowire Arrays," Angew. Chem. Int. Ed., 49, 6830-6835 (2010); U.S. Pat. No. 8,010,591 to Mojarradi et al, "Four-Gate Transistor Analog Multiplier Circuit;" and Haick et al, "Electrical Characteristics and Chemical Stability of Non-Oxidized Methyl-Terminated Silicon Nanowires," J. Am. Chem. Soc. 128, 8990-8991 (2006).

SUMMARY OF THE INVENTION

An aspect of some embodiments of the invention concerns a multi-gate field effect transistor (FET) with a conducting channel that acts like a virtual buried nanowire, whose conductivity is sensitive to a local concentration of molecules from a gas or liquid sample adhering to a surface of the FET, and whose transverse position is controllable by the gates, allowing the FET to function as a molecular sensor with improved sensitivity.

There is thus provided, in accordance with an exemplary embodiment of the invention, a system for sensing molecules in a gas or liquid sample, comprising:
  a) at least one multi-gate field effect transistor, comprising:
    1) a piece of semiconductor with an active region extending between a source region and a drain region, and left and right lateral regions extending along the active region on different sides;
    2) left and right lateral gate electrodes that respectively produce an electric field in the left and right lateral regions, creating a conducting channel in the active region when appropriate voltages are applied to them, a position of the conducting channel depending on the applied voltages;
    3) a sensing surface adjacent to the active region, that the molecules adhere to, a local concentration of the adhering molecules near the position of the conducting channel affecting its conductivity; and
  b) a controller adapted to successively apply different voltages to the lateral gate electrodes of the transistor, and move the conducting channel to a plurality of different positions, and at each position to measure its conductivity.

Optionally, the sensing surface is coated with a ligand that binds specifically to the molecules that are being sensed.

Optionally, the source region and drain region are doped with dopants of a same sign, and the left and right lateral regions are doped with dopants of an opposite sign to the source and drain regions.

Optionally, the active region is doped with a dopant of the same sign as the source and drain regions.

Optionally, the concentration of dopants of the lateral regions extends into the active region, falling off gradually over a scale length greater than the width of the conducting channel.

There is further provided, according to an exemplary embodiment of the invention, a method of manufacturing the field effect transistor in the system according to an embodiment of the invention, comprising heat treating the transistor under conditions such that some of the dopants from the left and right lateral regions diffuse into the active region, reducing an effective width of the active region by at least 30% at its narrowest point, but not reducing the effective width to zero at any point.

Optionally, the active region is narrower than 1 micrometer between the left and right lateral regions.

Optionally, the field effect transistor also comprises a back gate electrode, located in a direction away from the sensing surface and separated from the active region at least by an insulator layer, a voltage of the back gate electrode affecting one or both of an average distance and a range of distance of the conducting channel from the sensing surface.

Optionally, the controller is adapted to determine a concentration of adhering molecules adjacent to each of the positions of the conducting channels, from the conductivity measured at each of the positions.

Optionally, for at least one choice of gate electrode voltages, the system has a width of the conducting channel and a distance of the conducting channel from the sensing surface such that an equilibrium concentration of the adhering molecules can be determined when a concentration of the molecules in air that the sensing surface is exposed to is only 100 parts per million.

In an embodiment of the invention, the at least one field effect transistor comprises a plurality of field effect transistors, and the controller is adapted to change the position of the conductive channel in each transistor and to measure its conductivity at a plurality of different positions, to find a greatest concentration of adhering molecules near any of the positions, for each transistor, and to find an average over the transistors of the greatest concentrations of adhering gas molecules.

Optionally, the system is for use as an electronic nose for sensing a plurality of different types of molecules, and the at least one field effect transistor comprises a plurality of field effect transistors with sensing surfaces having different chemical properties, causing them to have different relative tendencies for the different molecules to adhere to them, and the controller is adapted to change the position of the conducting channel and determine a concentration of adhering molecules near each of the positions of the conducting channels, from the conductivity measured at each of the positions, for each transistor, and to find the type of molecules present by comparing a pattern of the concentrations of molecules adhering to each field effect transistor, to an expected pattern of concentrations of adhering molecules for each of the types of molecules.

Optionally, the field effect transistor also comprises a dielectric layer situated over the active region, and the sensing surface comprises a surface of the dielectric layer.

Optionally, the sensing surface of the transistor comprises an exposed surface of the active region.

Optionally, the semiconductor comprises silicon, and the exposed surface of the active region comprises methyl-terminated silicon.

Optionally, the sensing surface is adapted for exposure to a gas sample.

Alternatively, the system also comprises a reservoir adapted for holding a liquid sample and for exposing the sensing surface to the liquid sample.

There is further provided, in accordance with an exemplary embodiment of the invention, a method of sensing molecules in a gas or liquid sample with a multi-gate field effect transistor having a conductive channel connecting a source region to a drain region, a position of the conductive channel in a lateral direction controllable by changing two lateral gate voltages, and the conductivity of the conducting channel affected by the molecules adhering to a sensing surface of the transistor at a position near the conducting channel, the method comprising:

a) exposing the sensing surface to the gas or liquid sample;
b) changing the position of the conducting channel in the lateral direction, and measuring a conductivity of the channel at a plurality of positions of the channel; and
c) detecting the molecules by observing a change in conductivity of the conducting channel when it is in a position such that it passes close to one of the adhering molecules, or close to a fluctuation in a concentration of the adhering molecules on the sensing surface.

Optionally, the multi-gate field effect transistor is a field effect transistor comprising a back gate electrode that affects one or both of an average distance and range of distance of the conducting channel from the sensing surface, the method also comprising adjusting a voltage of the back gate electrode to improve a sensitivity of the conductivity of the conducting channel to the adhering molecules.

Optionally, changing the two lateral gate voltages affects a cross-sectional area of the conducting channel, a cross-sectional shape of the conducting channel, or both, at least partly independently of the position of the conducting channel in the lateral direction, as well as affecting the position of the conducting channel in the lateral direction.

Optionally, changing a position of the conducting channel in the lateral direction comprises keeping the two lateral gate voltages at values such that the conducting channel has a width in the lateral direction no greater than 50% of a full range of the positions that the conducting channel can move to in the lateral direction.

Optionally, changing a position of the conducting channel in the lateral direction comprises keeping the two lateral gate voltages at values such that the conducting channel has a width in the lateral direction no greater than 200 nanometers.

Optionally, the sample comprises a gas sample.

Alternatively, the sample comprises a liquid sample, and exposing the sensing surface to the liquid sample comprises holding the liquid sample in a reservoir.

There is further provided, according to an exemplary embodiment of the invention, a method of moving a conducting channel in a multi-gate field effect transistor with an active region between a source region and a drain region, and at least lateral gate electrodes that create a depletion region in part of the active region, the method comprising:

a) setting voltages of the gate electrodes to create a non-depleted conducting channel, narrower than the active region, connecting the source and drain regions through the active region; and
b) changing voltages of the lateral gate electrodes to move the conducting channel to different positions in a direction transverse to its length.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 3D-3F schematically show a cross-section of the sensor in FIGS. 1 and 2, seen from above, not drawn to scale, showing the conducting channel moved to different lateral positions by changing the lateral gate voltages;

DESCRIPTION OF SPECIFIC EMBODIMENTS OF THE INVENTION

Figure 1:
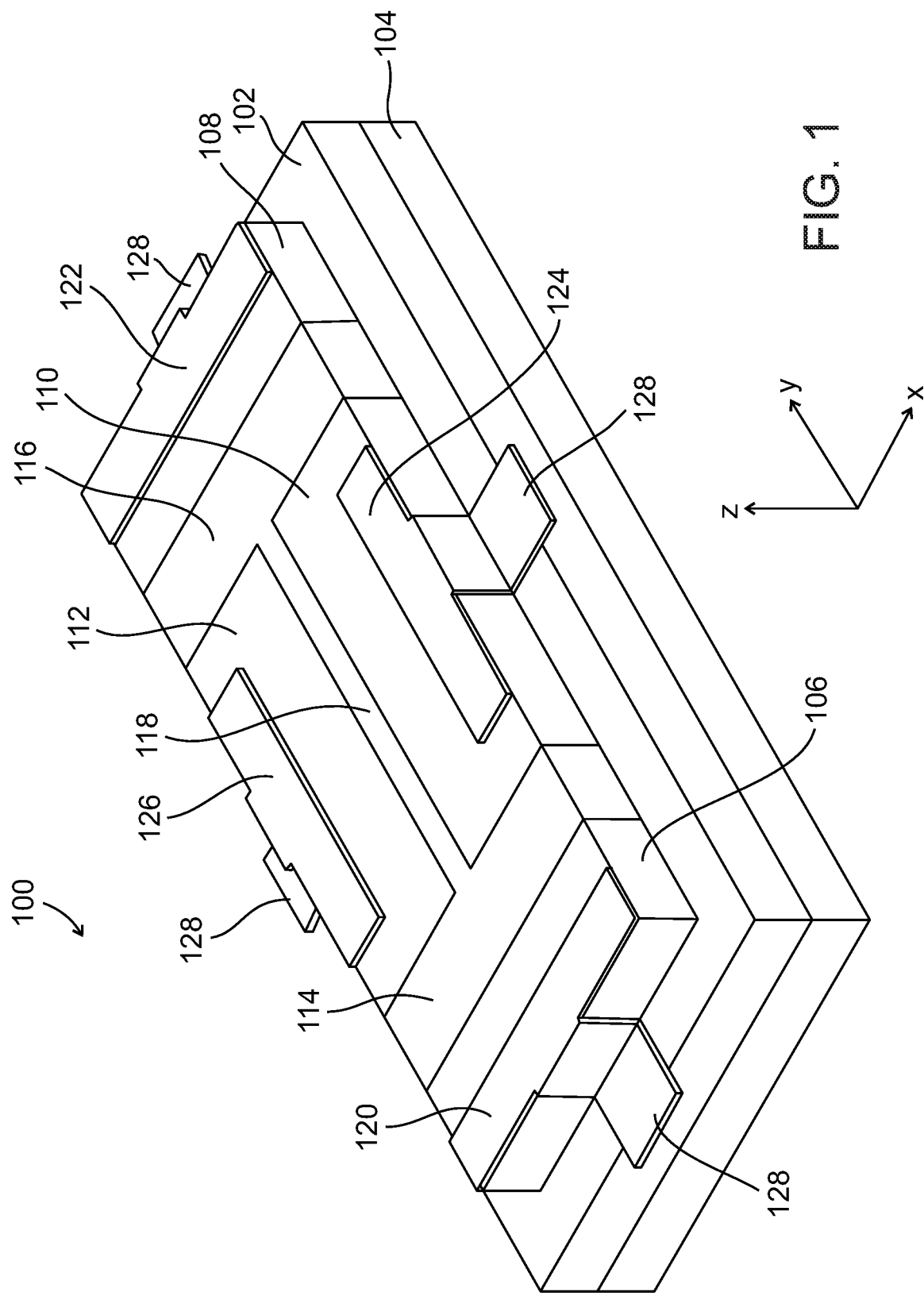
FIG. 1 schematically shows a perspective view of a virtual buried nanowire gas sensor, according to an exemplary embodiment of the invention.

The present invention, in some embodiments thereof, relates to a semiconductor chemical sensor and, more particularly, but not exclusively, to a gas sensor based on a field effect transistor.

An aspect of some exemplary embodiments of the invention concerns a multi-gate field effect transistor (FET) used for sensing molecules in a gas or liquid sample. The molecules adhere to an exposed surface of the FET, and affect the conductivity of a conducting channel going through the active region, which acts like a virtual buried nanowire, connecting a source region to a drain region. Lateral gate electrodes are optionally used to control a position of the conducting channel in a direction transverse to the length of the conducting channel. By measuring the conductivity of the conducting channel as its position is varied in the transverse direction, fluctuations in the concentration of adhering molecules can be detected, due for example to the small number of molecules, potentially making the sensor much more sensitive than a FET with a conducting channel that does not change its position, or to a molecular sensor using a real nanowire made of a different material and buried in the silicon at a fixed position. For example, in some embodiments of the invention, the sensor produces a response signal that depends on the conductivity of the conducting channel at a position of the conducting channel where the concentration of adhering molecules is greatest. Such a multi-gate FET molecular sensor using a virtual buried nanowire is also potentially much cheaper to mass produce than a conventional nanowire molecular sensor using a real buried nanowire. For example, it could be produced with conventional high volume, low cost CMOS manufacturing methods, since, optionally, no low-dimensional design rules are needed.

Other potential advantages of a virtual buried nanowire molecular sensor, over conventional nanowire molecular sensors, include increased SNR, enhanced gain, enhanced resolution, and faster device characterization and development. For conventional buried nanowire based sensors the dimensions of the nanowire need to be optimized in accordance with the organic system to be detected. This implies a lengthy characterization and development phase where nanowires of various compositions and dimensions need to be tested. In the virtual buried nanowire approach, the device is optionally fabricated only once. The optimization of the device for use in detecting a specific analyte is optionally accomplished by adjusting the gate voltages to produce virtual nanowires of different cross-sectional areas and shapes, and testing them.

The virtual buried nanowire molecular sensor is optimized, in different embodiments of the invention, to sense different analytes, for example, for medical diagnostic applications, for environmental applications, for military applications, or for other applications.

An aspect of some embodiments of the invention concerns a multi-gate FET with a virtual buried nanowire, in which the conducting channel is made narrower by increasing a dopant concentration in the active region, while using a heat treatment to cause dopants of the opposite sign to diffuse from the lateral gate regions part way into the active region from the sides. This makes the active region effectively narrower, while avoiding breakdown at the PN junctions between the lateral regions and the active region, and potentially with little or no reduction in the carrier density in the conducting channel. If the FET is used as a molecular sensor, with the conducting channel scanned laterally across the active region, the narrower channel potentially gives the sensor increased sensitivity, resolution, and/or SNR.

U.S. Pat. No. 8,007,727, to Shalev et al, "Virtual semiconductor nanowire, and method of using same," describes a multiple-gate field-effect transistor that includes a fluid in a top gate, two lateral gates, and a bottom gate. The multiple-gate field-effect transistor also includes a patterned depletion zone and a virtual depletion zone that has a lesser width than the patterned depletion zone. The virtual depletion zone width creates a virtual semiconductor nanowire that is lesser in width than the patterned depletion zone. This patent has a common inventor with the present application, but a different assignee.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1 shows an exemplary multi-gate FET 100, comprising a semiconductor layer built on top of an insulator layer 102, for example a buried oxide (BOX) layer of silicon oxide, optionally on top of a substrate 104, optionally made of the same material as the semiconductor layer, for example silicon. The semiconductor layer over the insulator layer is sometimes referred to herein as an SOI (silicon on insulator) layer, although other semiconductor materials are used instead of silicon in some embodiments of the invention, and materials other than silicon oxide are optionally used for the insulator layer. It should be understood that terms such as "on top of," "above," and "over," as used herein, refer to a direction that is shown as vertical in the drawings, but need not be literally vertical with respect to gravity; generally the device may be oriented in any direction with respect to gravity, without affecting its operation.

The semiconductor layer comprises a source region 106 at one end, and a drain region 108 at the other end, both doped with an implant of the same charge, for example an N implant. A right lateral gate region 110 and a left lateral gate region 112 are both doped with an implant of an opposite charge to the implant of the source and drain regions, for example a P implant. Alternatively, the source and drain regions are doped with a P implant and the gate regions are doped with an N implant. The rest of the semiconductor layer comprises a portion 114 adjacent to the source region, a portion 116 adjacent to the drain region, and a narrower active region 118 connecting the source region to the drain region. Portions 114 and 116, and active region 118 are optionally doped with an implant of the same sign charge as the implant of the source and drain regions, but are less strongly doped than the source and drain region. A source electrode 120 is connected to source region 106, a drain electrode 122 is connected to drain region 108, a right lateral gate electrode 124 is connected to right gate region 110, and a left lateral gate electrode 126 is connected to left gate region 112. Connectors 128 allow the electrodes to be connected to an external circuit which can control the voltage on each of the electrodes, and can measure the current between the source and drain electrodes.

Optionally, there is a back gate electrode, not shown in FIG. 1, attached to the bottom of substrate 104, or to the bottom of insulator layer 102 if there is no substrate 104 beneath the insulator layer. The presence of insulator layer 102 between the back gate electrode and the other electrodes makes it possible for the back gate electrode to affect the electric field and hence the carrier distribution in the active region, without drawing any current. Substrate layer 104 may be present as a result of the method of manufacture, in some methods of manufacturing FET 100.

Optionally, there is a gate dielectric layer, not shown in FIG. 1, above active region 118. The gate dielectric is optionally made of silicon oxide. Alternatively, other materials are used for the gate dielectric, including for example any of $HfO_2$, $Si_3N_4$, $Al_2O_3$, and $Ta_2O_5$.

It should be understood that the FET need not have the rectilinear geometry shown in FIG. 1, with the active region oriented along the y-direction, the lateral gate regions surrounding it in the x-direction, and the different layers arranged in the z-direction. Instead, the FET may be curved or twisted in any way, for example with the active region C-shaped, or S-shaped, or with the layers having surface curvature, as long as certain features are present, for example a path through the active region connects the source and drain regions, and the lateral gate regions are adjacent to the active region on its sides. However, a rectilinear geometry potentially makes the FET easier to manufacture by conventional manufacturing methods for semiconductor devices. The gate electrodes, which generally do not have substantial current running through them in normal operation, need not be in physical contact with the semiconductor layer or insulator layer, but could be separated from them by an air gap, although for reasons of mechanical strength it is potentially advantageous to have any electrodes in direct contact with semiconductor or insulator.

Figure 2:
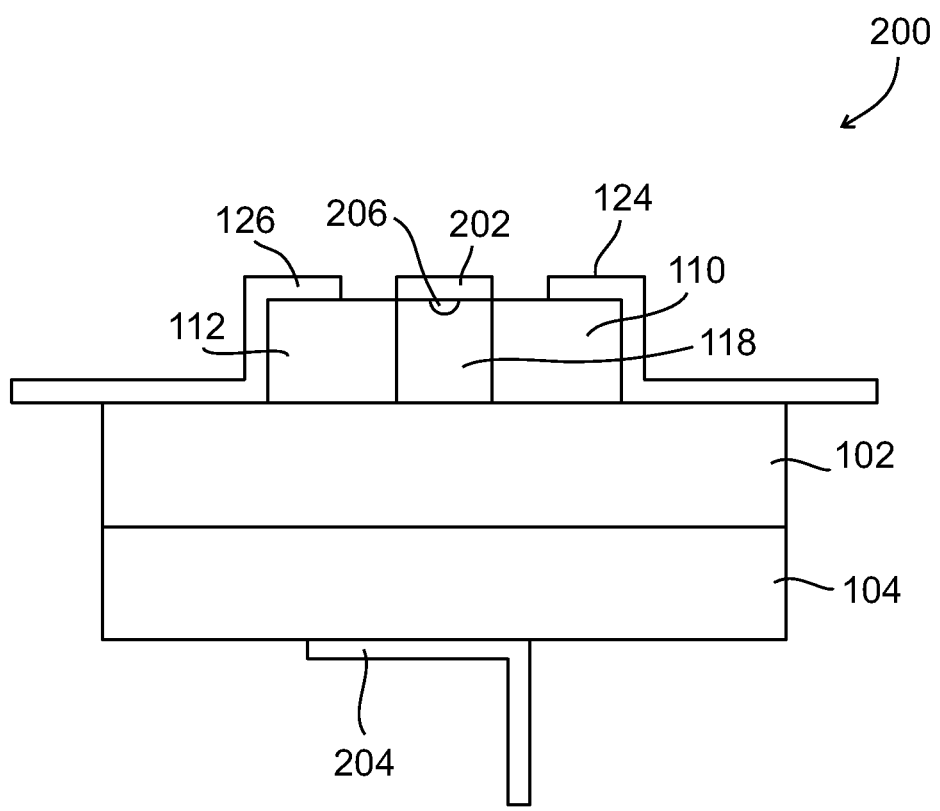
FIG. 2 schematically shows a cross section of the sensor in FIG. 1, perpendicular to the direction of the conductive channel in the middle of the channel, according to an exemplary embodiment of the invention.

FIG. 2 shows a cross-section 200 of FET 100, perpendicular to the direction from the source to the sink, and half way between the source and the sink. A dielectric layer 202 optionally covers active region 118, and a back gate electrode 204 is optionally attached to the bottom of substrate 104. A conducting channel 206, connecting the source and drain regions through active region 118, is created by applying appropriate voltages to the gate electrodes, a voltage $V_{Gj1}$ to the left gate electrode, a voltage $V_{Gj2}$ to the right gate electrode, and optionally a voltage $V_{Gb}$ to the back electrode. These voltages are measured, for example, relative to ground, and typically the source electrode is grounded. The voltage on the lateral gate electrodes creates an electric field in the semiconductor, which creates a depletion region, without charge carriers, at the interface of the lateral regions with the active region, extending into the active region, while the voltage on the back electrode creates a depletion region at the interface between the insulator layer and the active region, extending into the active region. For appropriate values of the gate voltages, the depletion region covers much of the active region, leaving only the relatively narrow undepleted conducting channel 206. When a voltage $V_{SD}$ is then applied between the source and the drain electrodes, a current flows between them which depends on the cross-sectional area of the conducting channel.

The FET functions as a gas sensor because the cross-sectional area of the conducting channel is sensitive to the charge of gas molecules adhering to the surface of the dielectric layer, sometimes referred to herein as a sensing surface. It should be understood that, although we describe herein embodiments of the invention that are used as gas sensors, other embodiments of the invention are used to detect molecules in a liquid sample, for example by adding a reservoir for holding a liquid sample to the top of the sensing surface. The charge of these adhering gas molecules changes the potential of the surface of dielectric layer 202, as if there were another gate electrode there, and this changes the cross-sectional area of the conducting channel. For this reason dielectric layer 202 is sometimes referred to herein as a gate dielectric, although in the embodiments described, there is optionally no physical gate electrode on top of the active region. Typically, for a given set of gate voltages, the current between the source and the drain is essentially zero up to a threshold voltage between the source and the drain, and increases rapidly above the threshold voltage. Optionally, the voltage between the source and the drain is set just below the threshold voltage in the absence of adhering gas molecules on the gate dielectric, so that even a small decrease in the threshold voltage, caused by a small number of adhering gas molecules, can greatly increase the current between the source and the drain, making the FET potentially a very sensitive detector of gas molecules. Typically, the threshold voltage between the source and the drain is between 10 mV and 100 mV, and the source to drain voltage is optionally kept at such low levels, much less than the lateral and back gate electrode voltages, which are typically a few volts.

Changing Lateral Position of Conducting Channel

Figure 3A:
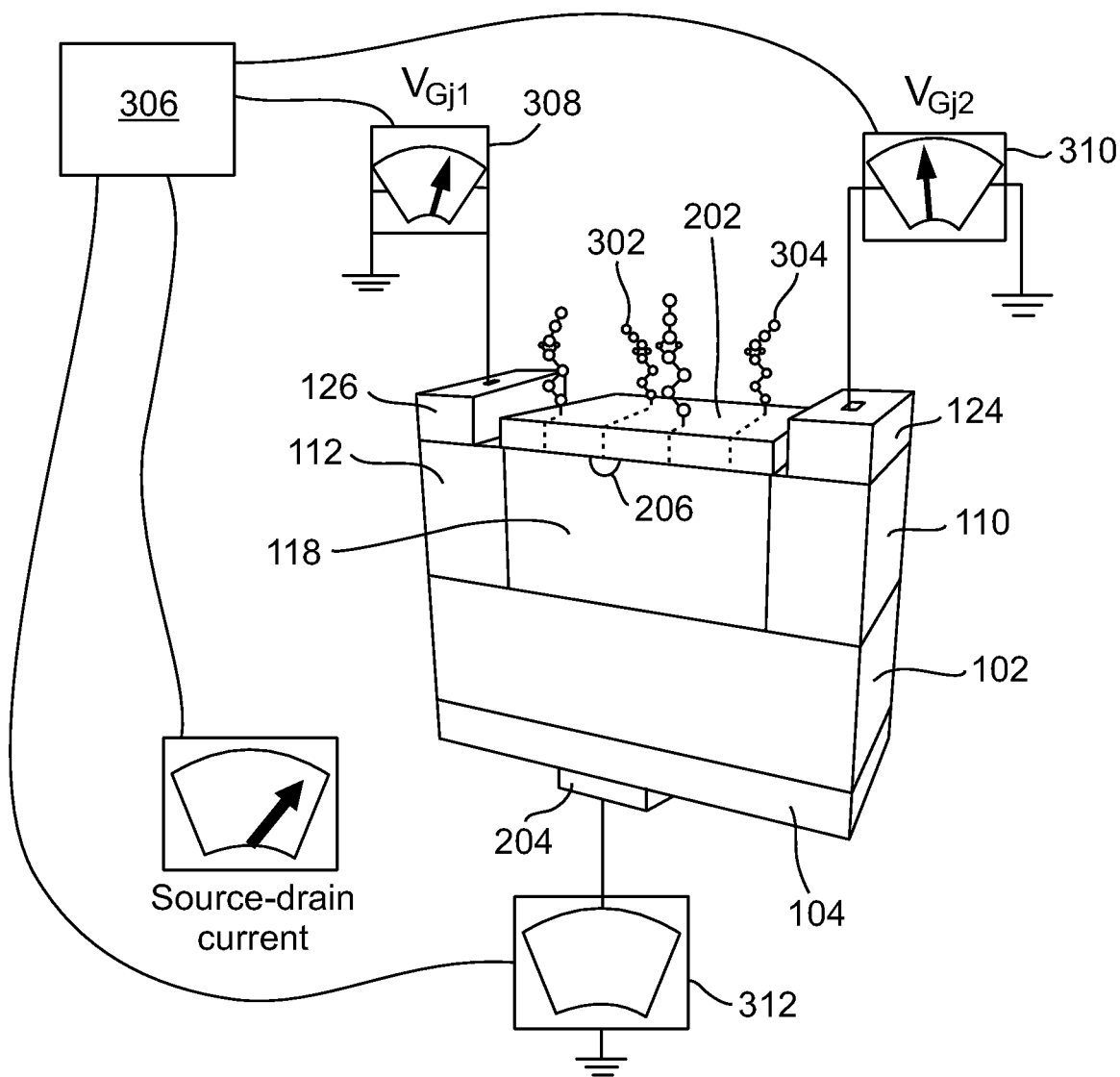
FIGS. 3A-3C schematically shows perspective views of a cross-section of the sensor in FIGS. 1 and 2, not drawn to scale, showing the conducting channel moved to different lateral positions by changing the lateral gate voltages, and the response of channel cross-section when the channel passes close to an adhering molecule.
Figure 3B:
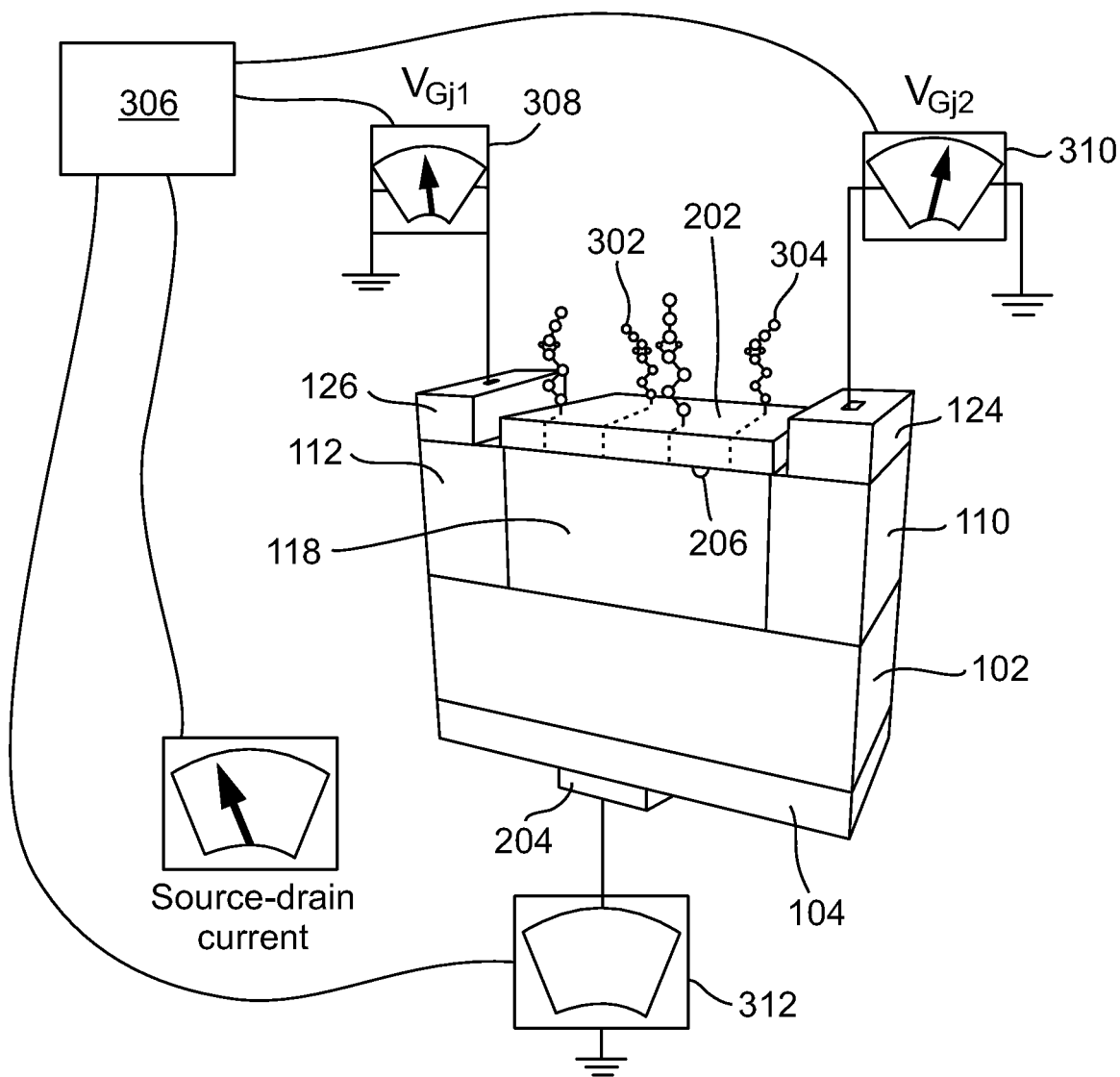
Figure 3C:
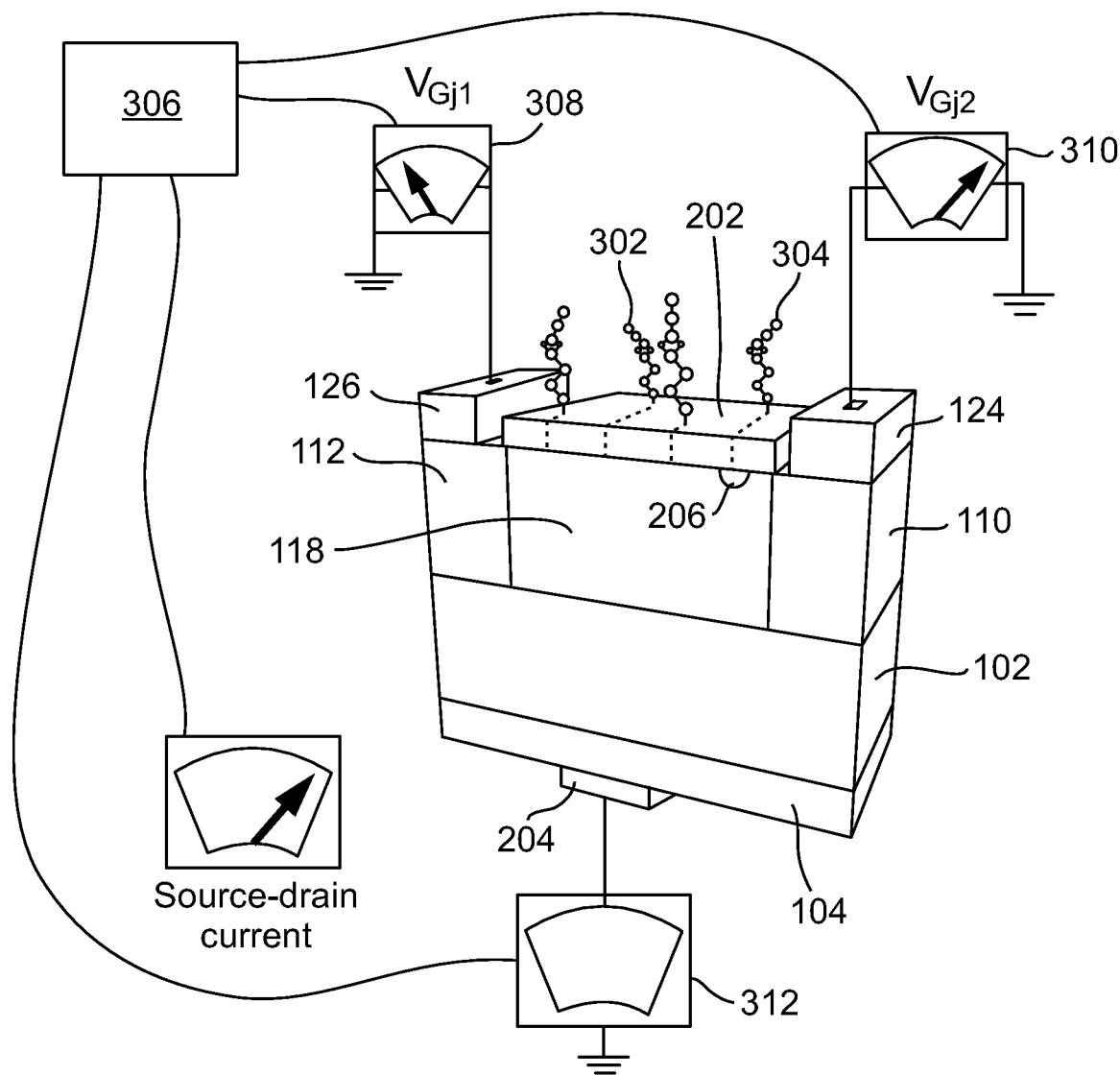

FIGS. 3A-3C illustrate how applying a different voltage on the left and right lateral gate electrodes optionally controls the lateral position of the conducting channel, and how changing the lateral position of the conducting channel is optionally used to increase the sensitivity of FET 100 as a gas sensor. In FIGS. 3A-3C, there is a relatively low concentration of gas above gate dielectric 202, and only a few gas molecules adhere to the surface. The left and right gate electrodes are optionally kept at voltages such that the conducting channel is very narrow, for example narrower than the width of the active region by a factor of 5, 10, 20, 50, or a lower, higher or intermediate value, and at a given lateral position of the conducting channel, there is less than one molecule, on average, adhering directly above any part of the conducting channel. In absolute dimensions, the width of the conducting channel is, for example, 500 nm, 200 nm, 100 nm, 50 nm, 20 nm, 10 nm, 5 nm, or a lower, higher, or intermediate value. As used herein, the width of the conducting channel means the full-width, in the y direction, at half-maximum of the carrier density.

As the lateral position of the conducting channel is scanned from left to right, by changing the voltage of the left lateral electrode relative to the voltage of the right lateral electrode, the cross-sectional area of the channel increases whenever it passes close to an adsorbed molecule. For example, in FIG. 3A, the channel passes under gas molecule 302, and its cross-sectional area is relatively large. In FIG. 3B, the channel does not pass close to any gas molecules, and its cross-sectional area is smaller. In FIG. 3C, the channel passes close to gas molecule 304, and its cross-sectional area increases again. In other embodiments of the invention, the current decreases, instead of increasing, when the conducting channel passes near an adhering gas molecule. By scanning the conducting channel across the active region, and measuring the current between the source and the drain at each lateral position of the channel, an accurate determination may be made of the density of gas molecules adhering to the gate dielectric. If the current between the source and drain were only measured at a fixed lateral position of the conducting channel, it would not be possible to do this, because the current would likely either be very small, corresponding to no adhering gas molecules, if the channel did not happen to pass close to any gas molecules, or very large, corresponding to a much higher density of adhering gas molecules than are actually present, if the channel happened to pass close to one of the gas molecules.

FIGS. 3D, 3E and 3F respectively show a cross-section of the semiconductor layer as seen from above, at the surface of the semiconductor layer or at a depth below the surface where conducting channel 206 is located, at three different positions of the conducting channel. Active region 118 and conducting channel 206 are not necessarily drawn to scale, but are shown wider than they typically are relative to the dimensions of the source, drain and lateral gate regions, so that the change in position of the conducting channel may be clearly seen. It should be noted that, as long as the FET is operated with source to drain voltage much less than the voltage between the source and the lateral and back gate electrodes, for example less by a factor of 10 or 100, then the conducting channel will generally be very uniform in cross-section along the active region between the lateral regions, as shown in FIGS. 3D-3F, although the conducting channel may fan out beyond the ends of the lateral regions.

In order to scan the conducting channel laterally across the active region, the lateral gate voltages, and optionally the back gate voltage, are controlled by a controller 306, which controls a power supply 308 that provides the left lateral gate voltage, a power supply 310 that provides the right lateral gate voltage, and optionally a power supply 312 that provides the back gate voltage, all relative to ground which is, for example, connected to the source electrode. Controller 306 optionally adjusts the gate voltages to keep the depth and cross-sectional dimensions of the conducting channel substantially constant as its position moves laterally across the active region, for example by running software that implements a control algorithm, or by using an electronic circuit that produces the right relationship between the gate voltages. The relationship between the different gate voltages that will accomplish this is found, for example, by simulations, as described below in FIG. 6, or by testing the FET in the absence of adhering gas molecules. The differences in source to drain current, at different lateral positions of the conducting channel, are then due primarily to differences in the concentration of gas molecules adhering above the conducting channel, and optionally the sensitivity of the sensor is optimized at all positions of the conducting channel.

Controller 306, or a different controller, optionally calculates an average density of adhering gas molecules on the gate dielectric surface, from the measured source to drain current as a function of lateral position of the conducting channel. For example, the average density is proportional to an average shift in threshold voltage, for all positions of the conducting channel, relative to the threshold voltage when there are no adhering gas molecules, and the constant of proportionality is calibrated using a sample with known concentration of the gas molecules. Alternatively, the number of adhering gas molecules is counted, by counting the number of times that the current in the conducting channel has a significant rise and fall as the conducting channel is scanned across the width of the active region, indicating that the channel has passed by one adhering gas molecule, and the density is found by dividing the number of adhering molecules by the surface area of the active region. The average shift in threshold voltage may produce a more accurate measure of the density of adhering gas molecules when the density is relatively high, or even when the density is relatively low if the change in threshold voltage as a function of channel position always has about the same width and height whenever the channel passes an adhering molecule. Counting the number of adhering molecules may produce more accurate results if there are relatively few adhering molecules, so that the conducting channel will usually not pass close to more than one adhering molecule at a time.

Figure 3G:
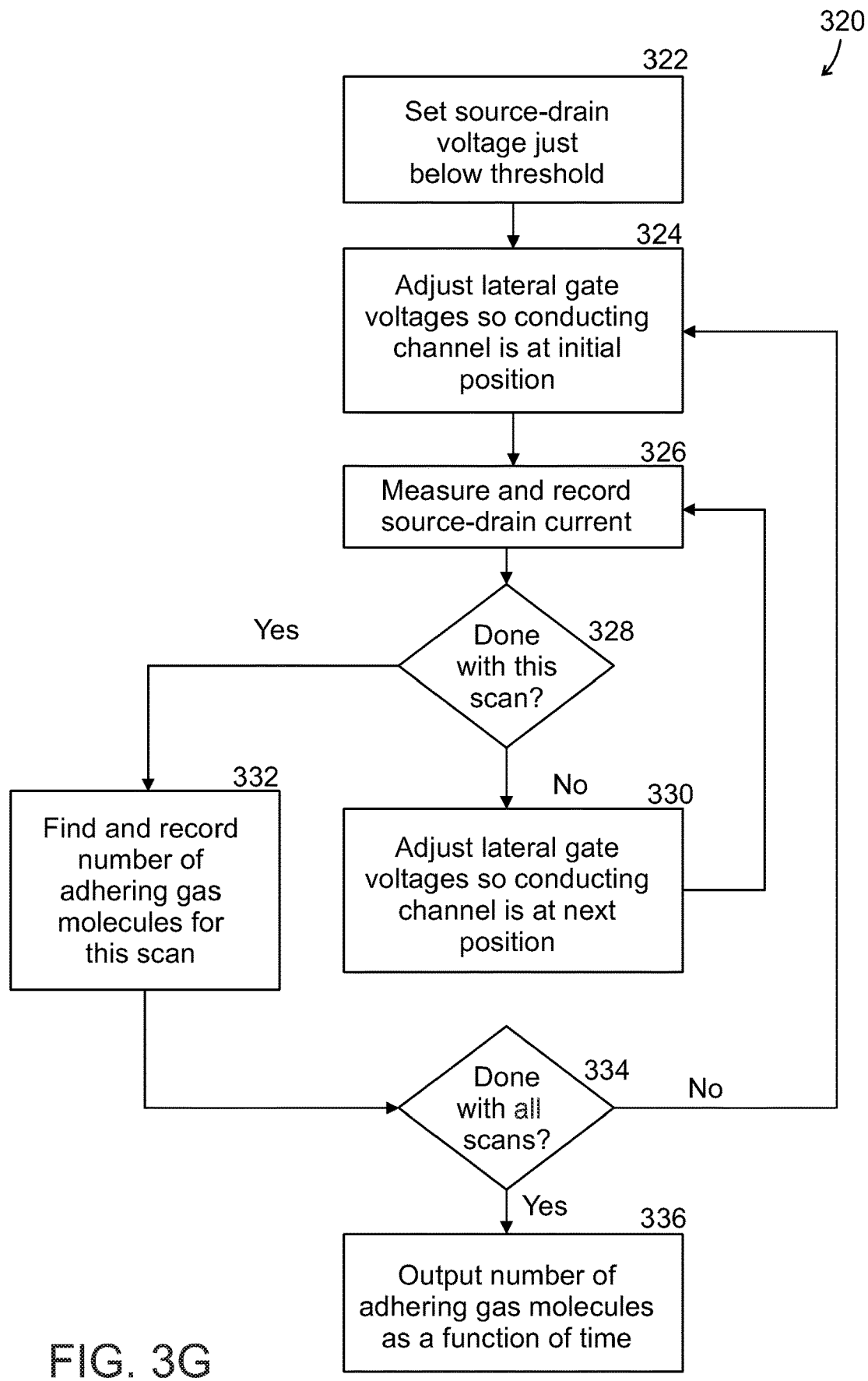
FIG. 3G shows a flowchart of a procedure for using the sensor shown in FIGS. 1 and 2, according to an exemplary embodiment of the invention.

FIG. 3G shows a flowchart 320 for a procedure used to measure the density of adhering gas molecules, according to an exemplary embodiment of the invention. At 322, the source to drain voltage is optionally set just below the threshold value in the absence of adhering gas molecules, so that the presence of an adhering gas molecule adjacent to the conducting channel will increase the source to drain current, by decreasing the source to drain voltage below the threshold voltage. In an embodiment where an adhering gas molecule decreases the current at a given voltage, the source to drain voltage is instead optionally set just above the threshold voltage, so that an adhering gas molecule will decrease the current. At 324 the lateral gate voltages, and optionally the back gate voltage, are set to a value for which the conducting channel will be at an initial position in the active region, for example all the way to one side of the active region in the lateral direction, or all the way at the beginning of a range of positions over which the conducting channel is to be scanned. At 326, while or after the gate dielectric is exposed to a gas sample, the source to drain current is measured and recorded. In another embodiment of the invention, instead of setting the source to drain voltage at a constant value at 322, and measuring changes in current caused by adhering gas molecules at 326, the source to drain current is kept at a constant value, for example at the maximum slope of current as a function of voltage just above the threshold voltage, and changes in voltage due to adhering gas molecules are measured. In effect, this is similar to measuring changes in the threshold voltage. Alternatively, a function of current and voltage is kept constant, and changes in a different function of current and voltage is measured.

At 328, if this scan is not done, then at 330, the lateral gate voltages, and optionally the back gate voltage, are adjusted to move the conducting channel to the next position. Optionally, this is done in such a way that the width and depth of the channel are not changed, or are changed very little, as described above. The position of the conducting channel need not change monotonically in time, but can jump around. However, it may be simplest, in interpreting the data and in controlling the voltages of the gate electrodes, to have the position of the conducting channel go sequentially from one side of the active region to the other side during a scan, making measurements at frequent intervals. After the gate voltages have been set to the new values at 330, moving the conducting channel to the new position, the source to drain current is measured and recorded again at 326. This loop is continued until the scan is done at 328, for example because the position of the conducting channel is all the way on the other side of the active region from what it was initially, or is all the way on the other side of the range of positions over which the conducting channel is being scanned.

When the scan is done, the number or density of adhering gas molecules is found at 332, from the data recorded at 326, for example source to drain current as a function of channel position at constant voltage, or the threshold voltage as a function of channel position, using any of the methods described above for finding the number or density of adhering gas molecules. At 334, if more scans are to be made, then the gate voltages are returned to the values that will put the conducting channel at its initial position, at 324, and a new scan is made. Optionally, scans are made repeatedly, while the gate dielectric is exposed to gas molecules, and the density of adhering gas molecules as a function of time. When all scans are done, at 334, the density of adhering gas molecules as a function of time is optionally supplied as output to a user, at 336. Typically, the density of adhering gas molecules will initially increase linearly with time, when the sensor is first exposed to the gas molecules, and will then saturate, as the gate dielectric becomes saturated with gas molecules, or as the rate of adherence of gas molecules is balanced by a rate of loss of adhering gas molecules from the surface. The concentration of gas molecules in a sample may be inferred from the initial rate of rise, and/or from the saturation level.

To estimate how much increase in sensitivity can be achieved by varying the position of the conducting channel, note that in general the sensitivity may become greater the narrower the effective width of the conducting channel, and assume that the noise level is low enough so that, for a conducting channel width of $W_c$, a single adhering gas molecule can be detected if it is within $W_c/2$ of the conducting channel. Then, if the width of the active region is $\Delta x$, on average the gas molecules could be detected, at a given position of the conducting channel, only if at least $\Delta x/W_c$ gas molecules were adhering to the upper surface of the FET. If the conducting channel were scanned across the active region, and the greatest response at any position were measured, then in principle even a single adhering gas molecule could be detected, an increase in sensitivity of $\Delta x/W_c$, which could be, for example, a factor of 5, or 10, or 20, or 30, or more. Although the greatest potential increase in sensitivity may occur, due to scanning the conducting channel, if a single adhering gas molecule could be detected directly over the conducting channel, some increase is sensitivity will occur even if, for example, a minimum of 2 or 3 adhering molecules are needed for detection at a given position of the channel, since there will be large fluctuations in the number of adhering molecules above the conducting channel, due to Poisson statistics, if the average number at a given position of the channel is a relatively small number such as 2 or 3. Relatively less increase in sensitivity due to scanning the conducting channel may occur, as the minimum number of adhering molecules, needed for detection at a given position, increases, and as $\Delta x/W_c$ decreases.

Gas Molecules Adhering Directly to Semiconductor with No Gate Dielectric

In some embodiments of the invention, the sensing surface that the gas molecules adhere to is, at least in part, an upper surface of the active region itself, and there need not be any dielectric layer over the active region. Optionally, in those embodiments, the semiconductor comprises silicon, and the upper surface of the active region, that the gas molecules adhere to, comprises methyl-terminated silicon, as described, for conventional silicon nanowires, by Haick et al, J. Am. Chem. Soc. 128, 8990-8991 (2006), cited above. Alternatively, the silicon is coated with a polar monolayer of organic molecules, as described by Paska and Haick, "Controlling properties of field effect transistors by intermolecular cross-linking of molecular dipoles," Appl. Phys. Lett. 95, 233103 (2009), and "Controlling surface energetics of silicon by intermolecular interactions between parallel self-assembled molecular dipoles," J. Chem. Phys. C 113, 1993-1997 (2009), by the same authors. Alternatively, the silicon is coated with dense hydrophobic organic hexyltrichlorosilane monolayers, that are especially suitable for nonpolar molecules, as described by Paska et al, "Enhanced sensing of nonpolar volatile organic compounds by silicon nanowire field effect transistors," ACS Nano 5, 5620-5626 (2011). Paska et al also describe other suitable coatings for this purpose.

Having the gas molecules adhere directly to the upper surface of the active region has the potential advantage of improving the sensitivity of the gas sensor. Using a dielectric layer, in particular a silicon dioxide dielectric layer, above the active region, has the potential advantage that the design is closer to the design of a conventional FET, and it may be possible to use more conventional manufacturing methods. Also, the technology of chemically modifying dielectric surfaces, for binding to specific gas molecules, may be more advanced than the technology of chemically modifying semiconductor surfaces, potentially allowing more flexibility in choosing which gas molecules are to be detected, for a sensor using a dielectric layer. But it should be understood that any of the devices and methods shown in the drawings could also be implemented without a dielectric layer above the active region, and having the gas molecules adhere directly to an upper surface of the active region.

Controlling Conducting Channel Dimensions

Optionally, the lateral gate electrodes also control a width of the channel in the transverse direction, at least partly independently of the position of the channel. This can be done if the voltage of the left and right lateral gate electrodes is controlled independently. Optionally the voltage of the back gate electrode, possibly together with the voltages of the lateral gate electrodes, controls a distance of the conducting channel from the sensing surface where the gas molecules adhere, and/or a range of distances of the conducting channel from the sensing surface. For the geometry shown in FIG. 2, this means controlling a vertical position and/or a vertical width of the conducting channel. This has the potential advantage that the conducting channel can be at a vertical position that is reasonably close to the top dielectric layer, for enhanced sensitivity, but not so close to the top dielectric layer that the sensor suffers from noise generated by noise centers at the interface between the semiconductor and the top dielectric layer. Optionally, the transverse and vertical width of the conducting channel, and/or the vertical position of the conducting channel, are set at values that give the gas sensor better sensitivity than it would have for other values. For example, the width of the channel, transversely and/or vertically, at its narrowest point, or on average over the length of the active region, is greater than 200 nanometers, or between 200 and 100 nanometers, or between 100 and 30 nanometers, or between 30 and 10 nanometers, or between 10 and 3 nanometers, or less than 3 nanometers, or more than 50% of the width of the active region in the transverse direction, or between 50% and 30% of the width, or between 20% and 10% of the width, or between 10% and 5% of the width, or less than 5% of the width. Optionally, the width of the active region in the transverse direction, at its narrowest point or on average over its length, is greater than 1 micrometer, or between 1 micrometer and 500 nanometers, or between 500 nanometers and 200 nanometers, or between 200 and 100 nanometers, or less than 100 nanometers. Optionally, the conducting channel is located vertically close to the top of the active region, i.e. close to the dielectric layer in the case where there is a dielectric layer, for example a distance of 200 nanometers, 100 nanometers, 30 nanometers, 10 nanometers, or 3 nanometers from the top of the active layer, or a greater, smaller, or intermediate distance, or a distance of 50%, 30%, 20%, 10% or 5% of the vertical thickness of the active region, from the top of the active region, or a greater, smaller, or intermediate distance.

It should be understood that if the active region is too wide, then the voltage that is applied to the lateral gate electrodes, in order to create a conducting channel of a given width, may be greater than the breakdown voltage of the PN junctions between the lateral gate regions and the active region. Making the conducting channel wider may make it less sensitive to adhering gas molecules. Making the conducting channel too narrow may result in it not having any carriers in it, on average, at a given time. The number of carriers can be increased by increasing the dopant concentration in the active region, but if the dopant concentration is too high, then the breakdown voltage of the PN junctions may decrease, and breakdown may occur at the voltage applied to the lateral gate electrodes. Making the active region longer may make the conducting channel more sensitive to adhering molecules, since a molecule adhering anywhere along the length of the conducting channel may significantly affect the conductivity. But increasing the length of the active region may also increase the threshold voltage between the source and drain, and if the voltage between the source and drain is not small enough relative to the lateral gate voltage, then the conducting channel may not be uniform in width along its length, and it may be less sensitive to adhering molecules. The dimensions and dopant concentrations given in the "Examples" section below represent a set of parameters that has been found to work well, both experimentally and according to simulations.

Embodiment with Narrower Active Region and Conducting Channel

In some embodiments of the invention, the FET is heat treated, causing dopants from the left and right lateral gate regions to diffuse part way into the active region from the sides, giving a portion of the active region, adjacent to the lateral gate regions, a net dopant concentration of the same sign as the lateral gate regions, and opposite to the rest of the active region. This diffusion of dopants in effect causes the lateral gate regions to extend part way into the active region, making the active region narrower in the lateral direction, and allowing the conducting channel to be narrower, as will be described below in the "Examples" section. The effective width of the active region is defined herein as the width of the part of the original active region where the net dopant concentration (the P dopant concentration minus the N dopant concentration) has the same sign as the net dopant concentration had originally in the active region, before the heat treatment, which is opposite to the sign of the net dopant concentration in the lateral gate regions. Optionally, the heat treatment reduces the effective width of the active region at its narrowest point by at least 20%, or at least 30%, or at least 40%, or at least 50%, or at least 60%, or at least 70%, or a greater than 70%. Optionally, the heat treatment is done at a temperature for which the diffusion rate of the lateral gate region dopant in the semiconductor, for example boron as a dopant in silicon, is the square of a desired diffusion distance divided by a desired time of the heat treatment. The desired time is, for example, less than 15 seconds, or between 15 and 30 seconds, or between 30 and 60 seconds, or between 60 and 90 seconds, or between 90 and 150 seconds, or between 150 and 300 seconds, or more than 300 seconds. The desired diffusion distance is, for example, less than 5% of the width of the active region, or between 5% and 10% of the width of the active region, or between 10% and 20%, or between 20% and 30%, or between 30% and 40%, or between 40% and 50%, or more than 50% of the width of the active region.

A potential advantage of reducing the width of the active region by using such a heat treatment, rather than making the active region narrower to begin with, even if that is possible with the lithography used, is that the net concentration of dopants changes more gradually between the lateral gate regions and the active region, making breakdown less likely at the PN junctions between the lateral gate regions and the active region. In some embodiments of the invention, the active region is doped at a higher concentration originally, so that, after the heat treatment, it still has a net dopant concentration at its center that is at a high enough level to produce a desired carrier density in the conducting channel, for example high enough to produce a carrier density greater than $10^{18}$ cm$^{-3}$, or greater than $5\times10^{17}$ or $3\times10^{17}$ or $2\times10^{17}$ or $1\times10^{17}$ cm$^{-3}$, even when the conducting channel is very narrow, for example narrower than 50 nm or 30 nm or 20 nm or 10 nm.

In an exemplary embodiment of the invention, the SOI layer is silicon, the lateral gate regions are doped with boron, the width of the active region is 400 nm, and the heat treatment is a temperature of 1050° C., and lasts for 75 seconds, causing boron from the lateral gate regions to diffuse far enough into the active region to reduce the effective width of the active region to only 90 nm at its narrowest point, and 130 nm at the top, adjacent to the gate dielectric. Optionally, the heat treatment is at a temperature below 900° C., or between 900° and 1000° C., or between 1000° C. and 1100° C., or between 1100° and 1200° C., or above 1200° C. Optionally, the heat treatment lasts for less than 15 seconds, or between 15 and 30 seconds, or between 30 and 60 seconds, or between 60 and 90 seconds, or between 90 and 150 seconds, between 150 and 300 seconds, or more than 300 seconds. To achieve a given amount of diffusion of dopants, less time may be needed if the temperature is higher, and the temperature and time of the heat treatment may be very different depending on the dopant used, since different dopants may diffuse at very different rates at a given temperature. Using a dopant that diffuses more easily has the potential advantage that the heat treatment may be less expensive because it takes less time and a lower temperature may be used. Using a dopant that diffuses less easily has the potential advantage that it may be easier to control the diffusion and to get repeatable results. Using a longer heat treatment at a lower temperature may also make the process more controllable and repeatable. But if the temperature is too low, or if the dopant has too low a diffusion rate, the time required to achieve a given degree of diffusion may be impracticably long.

Sensitivity of Gas Sensor

Optionally, the conducting channel is controlled to be narrow enough, and close enough to the dielectric layer, but not too close, so that the gas sensor has a sensitivity to gas molecules in air that the dielectric layer is exposed to, sufficiently high so that the sensor can detect less than 100 parts per million (ppm) of the gas, after exposure to the air for a long enough time so that the concentration of adhering gas molecules reaches an equilibrium, for example for at least several seconds, or at least several tens of seconds. Optionally, the sensitivity is sufficiently high to detect less than 30 ppm of the gas, or less than 10 ppm, or less than 3 ppm, or less than 1 ppm, or less than 300 parts per billion (ppb), or less than 100 ppb, or less than 30 ppb, or less than 10 ppb, or less than 3 ppb, or less than 1 ppb, or less than 0.3 ppb, or less than 0.1 ppb.

Chemical Treatment of Gate Dielectric

Optionally, the gate dielectric is chemically treated, for example, a SiO$_2$ gate dielectric is modified with APTMS, or with AUTES, or in other ways. Optionally, the gate dielectric is modified by coating it with a ligand, so that it binds specifically to the gas molecules being sensed, in a "lock and key" configuration. Alternatively, the gate dielectric is chemically treated with a ligand that does not bind only to the gas molecules being sensed. For example, the ligand also binds to one or more other gas molecules that are potentially present in an environment where the sensor is designed to be used. In some embodiments of the invention, referred to sometimes as an electronic nose or "e-nose," an array of FETs is used, with the gate dielectrics of the different FETs having different chemical treatments, and different types of gas molecules have different relative tendencies to bind to different FETs in the array, and/or different FETs in the array have different sensitivities to one type of molecule, even if that is the only type of molecule that the sensor is designed to detect. The type or types of gas present is then optionally determined from the signature of the response it produces from each of the FETs in the array, for example using an algorithm.

Use of Other Materials

The FET may use any of a variety of semiconductors for the active region, and any of a variety of dielectric materials for the gate dielectric, and for the insulator layer between the active region and back gate electrode if there is one. For convenience, the semiconductor may be referred to herein as "silicon" and the dielectric material may be referred to herein as "oxide," for example "gate oxide" or "buried oxide," or "silicon oxide," but it should be understood that other suitable materials may be used instead.

Fabrication Method

An exemplary method of fabrication of FET 100 begins with a silicon-on-insulator (SOI) wafer. A silicon island is optionally shaped, with the silicon around the island etched completely away until the buried oxide (BOX) is reached, as may be seen in FIGS. 1 and 2, where the silicon island is the semiconductor layer. In this method of fabrication, optionally there is no silicon substrate layer 104, but the insulator layer is the substrate. Alternatively, the silicon island may be grown, for example as polysilicon, on the insulator side of an SOI wafer, leaving the silicon layer as substrate 104 beneath the insulator layer, as in FIGS. 1 and 2. The silicon island has a length L along an axis shown as the y-axis in FIG. 1, and a width W along a lateral axis shown as the x-axis in FIG. 1. In an exemplary embodiment of the invention, a critical dimension of the device is the distance between the two lateral gate regions. This distance could is optionally defined with g-line lithography, i-line lithography or a smaller wavelength. In an exemplary embodiment of the invention, source and drain regions are created via implants, for doping of the silicon, on each end of the silicon island to allow for a conducting channel going between them, parallel to the y-axis. The left and right lateral gate regions are defined via implants on each side of the active region, including the conducting channel, in the x-direction. Optionally, the implants of the lateral gates are of opposite sign from that of the source/drain implants, i.e. if one of them is P then the other one is N. The active region is optionally implanted with the same species as the source/drain implants, i.e. both of them are P or both of them are N. In an exemplary embodiment of the invention, metal contacts are then created for the source and drain and the lateral gates, and optionally the back gate. Optionally, inter-layer-dielectric (ILD) and passivation are incorporated in order to isolate the contacts from the gas sample. A gate dielectric layer is optionally added on top of the conducting channel.

Depth of Conducting Channel

Nanowires inherently suffer from surface states. These surface states may entail degradation in sensor performance in terms of gain and SNR. In a virtual buried nanowire device, the conducting channel is optionally removed from the noise centers at the Si/SiO$_2$ interface by using the gate voltages to adjust the depth of the conducting channel, and adjusting the depth of the implants in the semiconductor, which potentially achieves greater gain and SNR for the sensor.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental and calculational support in the following examples.

Examples

Reference is now made to the following examples, which together with the above descriptions illustrate some embodiments of the invention in a non limiting fashion. The general silicon configuration of the virtual buried nanowire gas sensor was demonstrated experimentally for biological detection. In this experiment, the thickness of the SOI layer was 260 nm, with boron doping of $1.6 \times 10^{14}$ cm$^{-3}$, giving it a resistivity of 13 to 22 Ωcm. The thickness of the buried oxide was 1 µm. The thickness of the SiO$_2$ gate dielectric was 5 nm. The active region, including the wide portions adjacent to the source and drain regions, was doped with arsenic in the range of $1.6 \times 10^{17}$ cm$^{-3}$. The source and drain regions were doped with arsenic in the range of $5 \times 10^{19}$ cm$^{-3}$, and the lateral gate regions were doped with boron in the range of $5 \times 10^{19}$ cm$^{-3}$. The distance from source to drain region was 10 µm, and the length of the active region, defined as the length of the lateral gate regions, was 7 µm. The width of the active region was 400 nm.

Figure 4A:
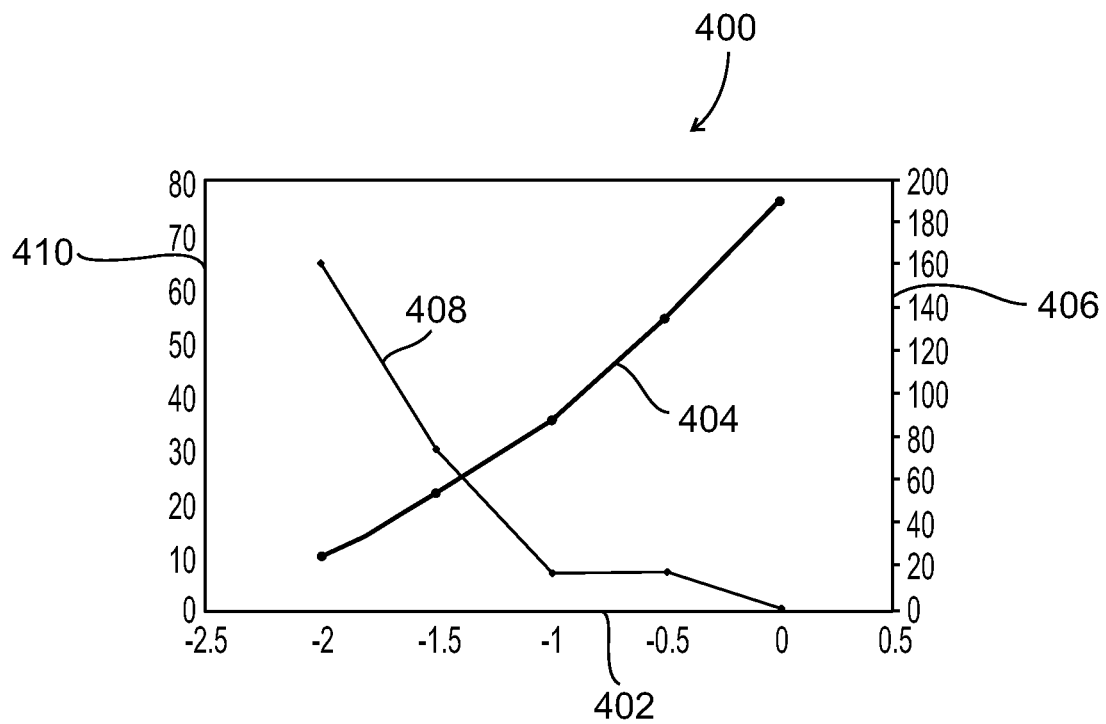
FIG. 4A shows a plot of simulation results for effective channel width, and test results for a shift in source to drain threshold voltage $\Delta V_T$, as a function of lateral gate voltage, for a virtual buried nanowire gas sensor similar to that shown in FIGS. 1 and 2, used for specific anti-troponin detection, in aqueous conditions and with a reference electrode, according to an exemplary embodiment of the invention.

In FIG. 4A, a plot 400 presents results for the specific detection of anti-troponin. Horizontal axis 402 shows a voltage $V_{Gj}$, in volts, applied to both the left and right lateral gate electrodes, relative to ground, with the source electrode grounded. The back gate electrode was kept at a voltage of −7 volts. Curve 404 plots the effective width $W_{eff}$ of the conducting channel, in nanometers, as a function of the lateral gate voltage, with the values shown on vertical axis 406 on the right side of the plot, in nanometers. Curve 408 plots the change in source to drain threshold voltage associated with the presence of anti-troponin, as a function of lateral gate voltage $V_{Gj}$, with the values shown on vertical axis 410 on the left side of the plot, in millivolts. Note that the narrower the conducting channel is, the higher is the shift in threshold voltage between the source and drain associated with the presence of anti-troponin.

Figure 4B:
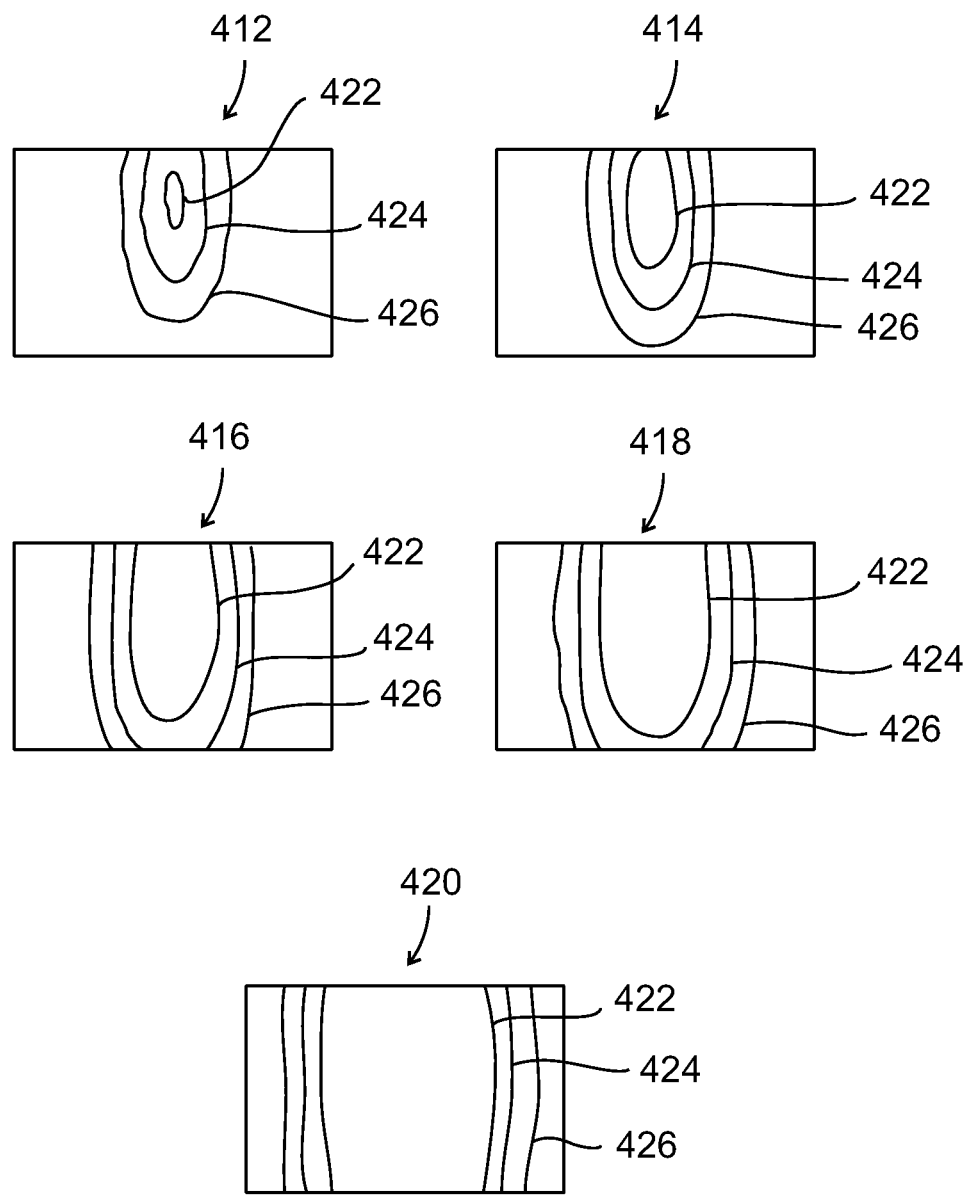
FIG. 4B shows contour plots of the carrier density in the active region, for different values of gate voltage, from a simulation of the sensor used for FIG. 4A.

FIG. 4B shows contour plots of the carrier density, in this case electron density, in a cross-section of the active region, which is 250 nm high and 400 nm wide, perpendicular to the direction of the conducting channel, half way between the source and the drain regions, for different values of the lateral gate voltage $V_{Gj}$. Plots 412, 414, 416, 418, and 420 respectively show the carrier density for $V_{Gj}$ equal to −2.0, −1.5, −1.0, −0.5, and 0.0 volts. Contours 422, 424 and 426 respectively correspond to carrier densities of $4 \times 10^{19}$ cm$^{-3}$, $2 \times 10^{16}$ cm$^{-3}$, and $1 \times 10^{13}$ cm$^{-3}$.

Figure 5:
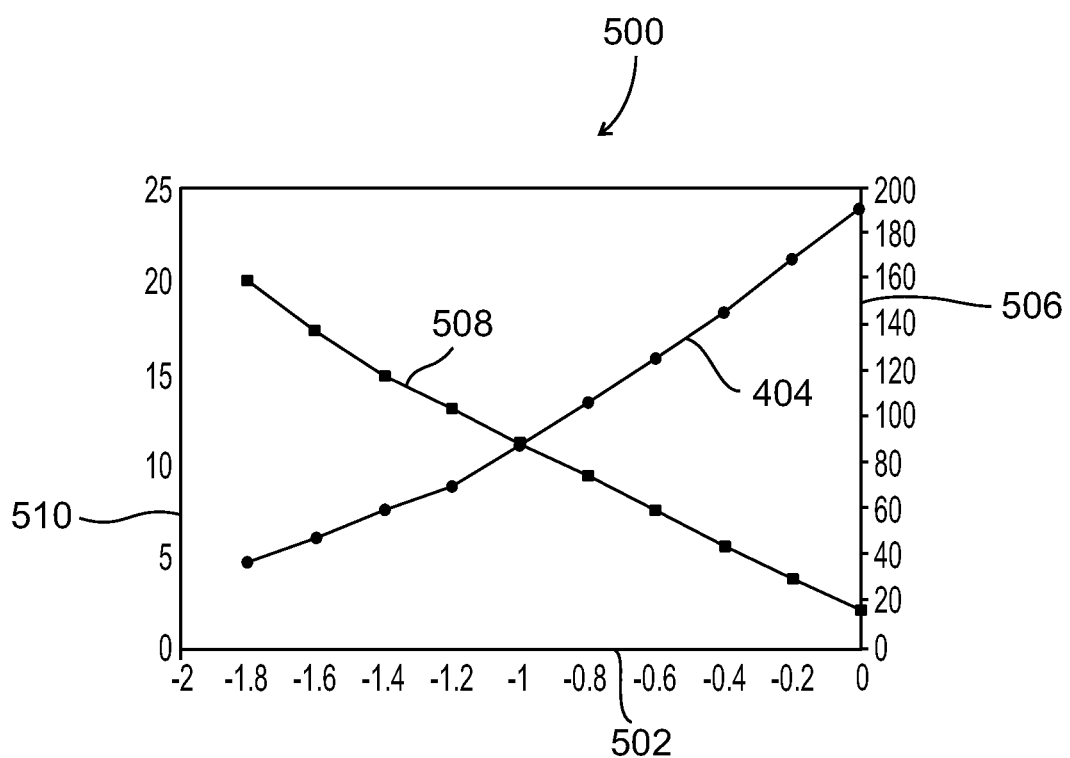
FIG. 5 is a plot of simulation results for conducting channel width $W_{eff}$, and shift in average potential of the upper surface of the active region, due to a given charge placed on top of the gate dielectric above the center of the conducting channel, as a function of lateral gate voltage $V_{Gj}$, for a virtual buried nanowire gas sensor similar to that shown in FIGS. 1 and 2, according to an exemplary embodiment of the invention.

Also, the principle of operation of the virtual buried nanowire gas sensor was simulated using 'Sentaurus' software, sold by Synopsys, Inc. The parameters used in the simulation were the same as the parameters described above for the experiment, except that the length of the active region and the lateral gate regions was only 3 µm, in order to save on computation time. A SiO$_2$ cubic of 10 nm side with fixed charge density of $10^{19}$ e·cm$^{-3}$ was placed at the center of the channel on top of a gate dielectric, in this simulation, to represent a molecule adhering at that location. The shift in the average potential of the SOI region due to the presence of the charge was calculated for various channel widths. The results are presented in FIG. 5, in a plot 500. As in plot 400, horizontal axis 502 shows the voltage $V_{Gj}$, in volts, applied to both the left and right lateral gate electrodes, relative to the source electrode which is grounded, and curve 504, which is in close agreement with curve 404 in plot 400, shows the effective width $W_{eff}$, in nanometers, of the conducting channel, as a function of $V_{Gj}$, with the values shown on vertical axis 506 on the right side of the plot. Curve 508 shows the change in average potential of the active region, associated with the presence of the 10 nm wide charged cube of $SiO_2$ representing an adhering gas molecule in the simulation, with the values, in millivolts, shown on vertical axis 510 on the left side of the plot. The average is taken over the full 400 nm width and 260 nm depth of the active region, and extending over the full length from source to drain regions. Note that the smaller the width of the conducting channel, the greater the change in average potential over the active region due to the presence of the simulated adhering molecule. The change in potential averaged only over the conducting channel, though not shown in FIG. 5, goes up even more dramatically, with narrower channel width.

Figure 6:
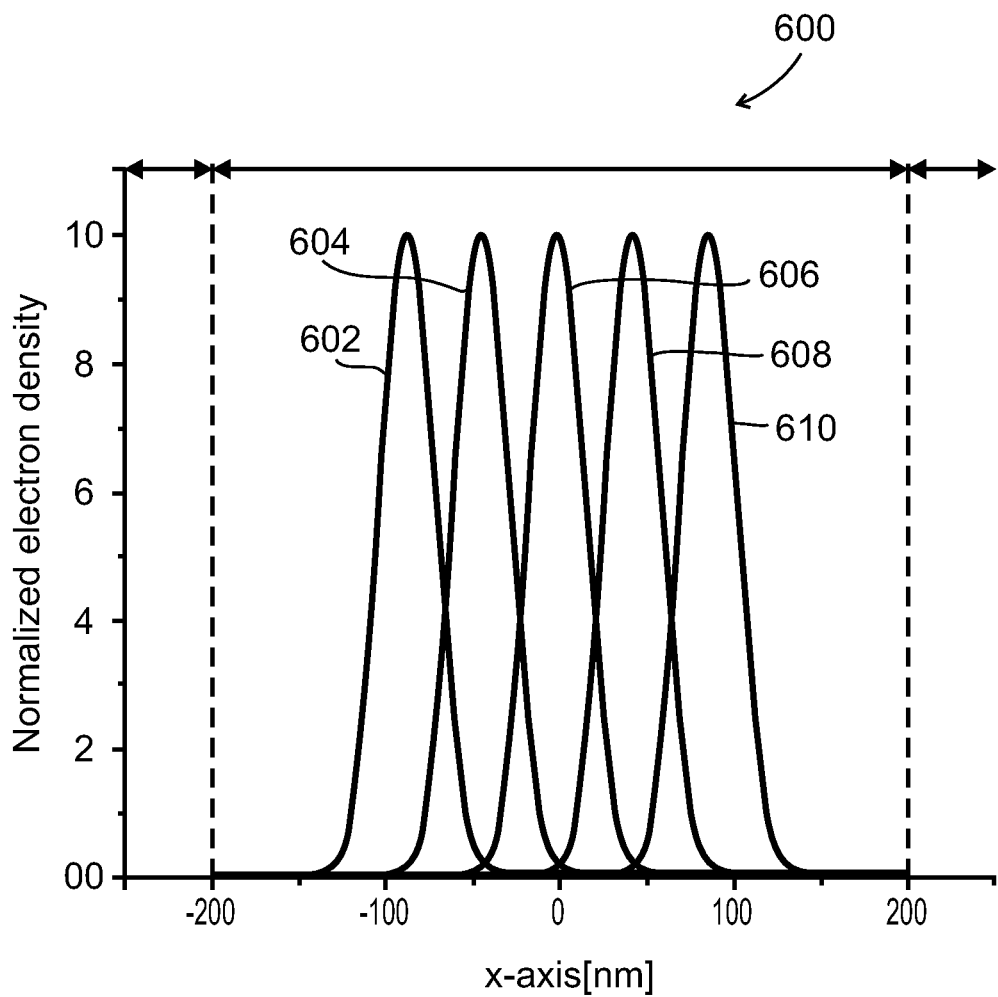
FIG. 6 is a plot of simulation results for the carrier density as a function of x, near the surface of the active region, for a carrier channel centered at five different lateral positions by changing the left and right lateral gate voltages, according to an exemplary embodiment of the invention.

FIG. 6 shows a plot 600, illustrating the results of a simulation of scanning the conducting channel across the active region by varying the voltage $V_{Gj1}$ on the left lateral gate electrode, and the voltage $V_{Gj2}$ on the right lateral gate electrode. In this simulation, the parameters were the same as for the experiment described above. Curve 602 shows the normalized carrier (electron) density as function of lateral position x in the active region, when $V_{Gj1}$=0 volts and $V_{Gj2}$=−5.16 volts. Curve 604 shows the carrier density when $V_{Gj1}$=−0.85 volts and $V_{Gj2}$=−3.43 volts. Curve 606 shows the carrier density when $V_{Gj1}$=−2.0 volts and $V_{Gj2}$=−2.0 volts. Curve 608 shows the carrier density when $V_{Gj1}$=−3.43 volts and $V_{Gj2}$=−0.85 volts. Curve 610 shows the carrier density when $V_{Gj1}$=−5.16 volts and $V_{Gj2}$=0 volts. By varying the left and right lateral gate voltages in this way, the position of the conducting channel moves from left to right, over a distance of 200 nm, while the width of the conducting channel remains constant at 100 nm. The active region extends from x=−200 nm to +200 nm.

Figure 7A:
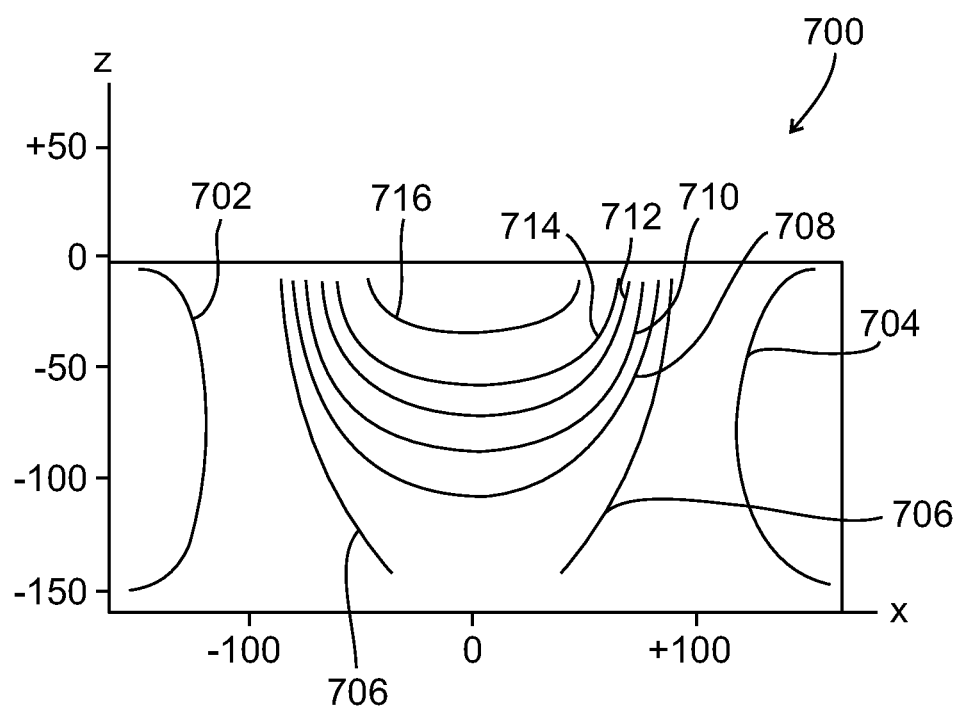
FIGS. 7A and 7B are simulation results showing contour plots of the carrier density in a cross-section of the active region, for two different values of the lateral gate voltages, showing how the channel width can be adjusted, for a virtual buried nanowire gas sensor similar to that shown in FIGS. 1 and 2, according to an exemplary embodiment of the invention.

FIG. 7A shows a contour plot 700, of the carrier density in the active region as a function of position in a cross-section perpendicular to the direction of the conducting channel, the y-axis, when the lateral gate voltages are both zero, according to a simulation. The values of x and z are given in nanometers. The parameters are similar to those of the experiment described above, except that the arsenic doping in the active region, still averaging $1.6 \times 10^{17}$ $cm^{-3}$, is not homogeneous, but is higher closer to the gate dielectric and lower closer to the insulator layer, which makes the conducting channel form adjacent to the gate dielectric.

Curves 702 and 704 in FIG. 7A respectively show the junctions of the active region with the left and right lateral gate regions. Curve 706 is the boundary of the depletion zone in the active region, where the carrier density goes to zero. Curves 708, 710, 712, 714, and 716 respectively show the contours for carrier density of $0.5 \times 10^{17}$, $1.0 \times 10^{17}$, $1.5 \times 10^{17}$, $2.0 \times 10^{17}$, and $2.5 \times 10^{17}$ $cm^{-3}$. The conducting channel is about 150 nm in diameter, a large fraction of the width of the active region, which is about 220 nm at its narrowest point.

Figure 7B:
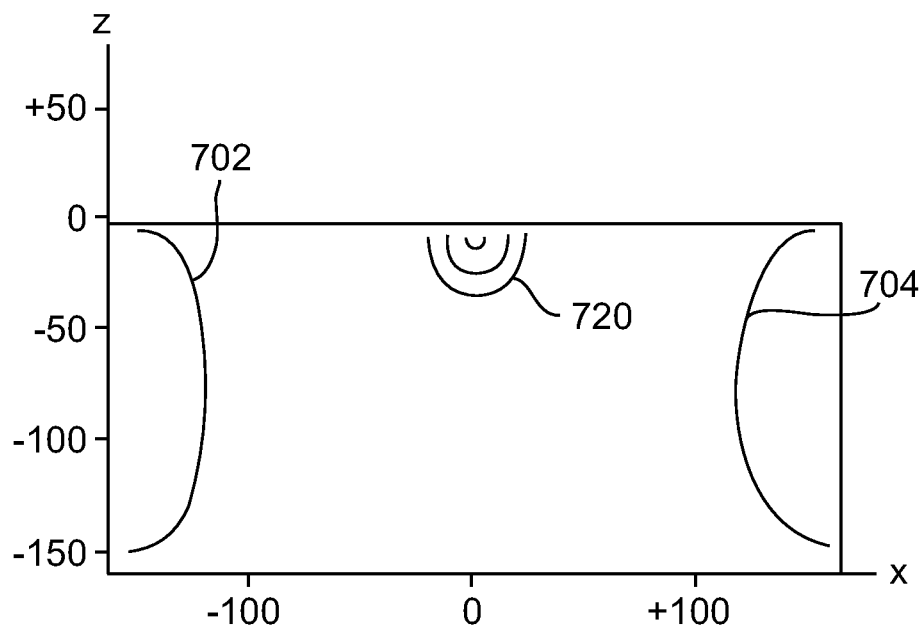

FIG. 7B shows a similar contour plot 718, for the case where the left and right lateral gate voltages are both −2.0 volts. Here curve 720 is the boundary of the depletion zone in the active region, where the carrier density goes to zero, and the two contours inside curve 720 are the contours for carrier density of $0.5 \times 10^{17}$ and $1.0 \times 10^{17}$ $cm^{-3}$. The conducting channel is now about 40 nm in diameter.

Figure 8A:
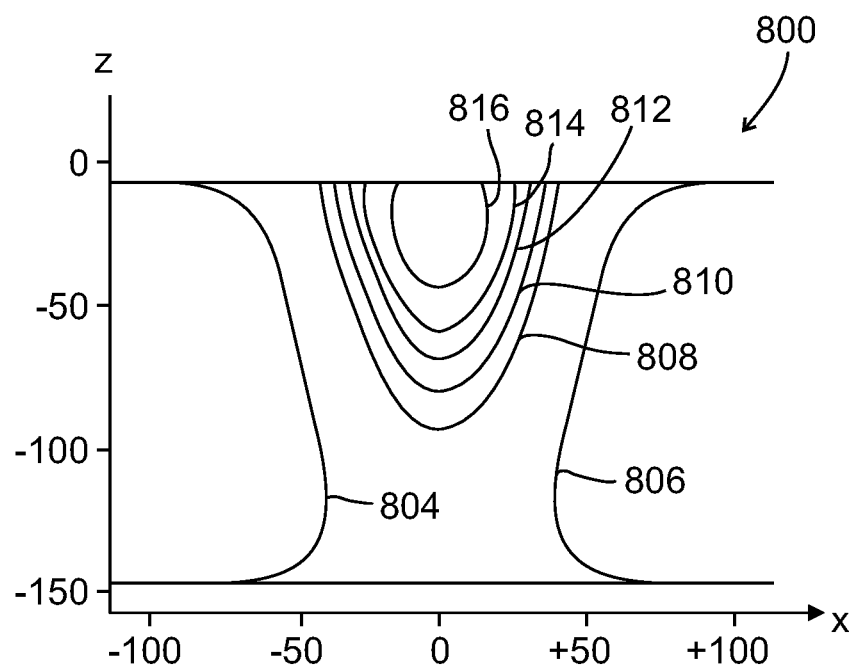
FIGS. 8A and 8B are simulation results of contour plots similar to those in FIGS. 7A and 7B, but for a virtual buried nanowire gas sensor in which heat treatment has been used to cause dopants from the lateral gate regions to move into the active region, making the active region narrower, and allowing the conductive channel to be narrower, according to an exemplary embodiment of the invention.
Figure 8B:
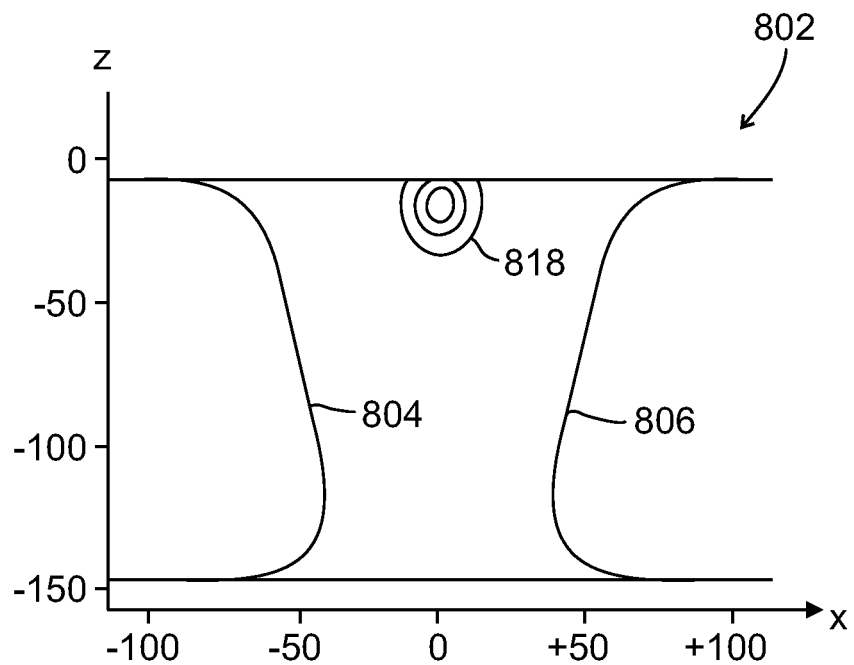

FIGS. 8A and 8B show contour plots 800 and 802 of carrier density in the active region, from a simulation, with parameters similar to those in the plots in FIGS. 7A and 7B, but for a case in which the FET has been heat treated, so that dopants from the lateral gate regions have diffused somewhat into the active region, and with a higher density of dopants implanted in the active region, $10^{18}$ $cm^{-3}$. The heat treatment, at a temperature of 1050° C., is applied for 75 seconds, causing boron to diffuse from the lateral gate regions into the active region.

Curves 804 and 806 in FIGS. 8A and 8B show the left and right boundaries of the effective active region, where the net dopant density still has the same sign as before the heat treatment. This effective active region has a width of only 90 nm at its narrowest point, but about 130 nm at the depth of the center of the conducting channel. FIG. 8A shows the case where the lateral gate voltages are both zero. Curve 808 is the boundary of the depletion zone in the active region, where the carrier density goes to zero. Curves 810, 812, 814, and 816 respectively are the density contours for $2 \times 10^{18}$, $4 \times 10^{18}$, $6 \times 10^{18}$ and $8 \times 10^{18}$ $cm^{-3}$. The conductive channel is about 90 nm wide. FIG. 8B shows the case where the lateral gate voltages are both −2.0 volts. Curve 818 is boundary of the depletion zone, and the two curves inside it are the density contours for $2 \times 10^{18}$ and $4 \times 10^{18}$ $cm^{-3}$. The conductive channel is only about 25 nm, much narrower than in FIG. 7B, without heat treatment of the FET.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for sensing at least one type of molecules in a gas or liquid sample, comprising:
   a) at least one multi-gate field effect transistor, comprising:
      1) a piece of semiconductor with a first region extending between a source region and a drain region, and left and right lateral regions extending along the first region on different sides;
      2) left and right lateral gate electrodes that respectively produce an electric field in the left and right lateral regions, creating a conducting channel in the first region when appropriate voltages are applied to them, a position of the conducting channel depending on the applied voltages;
      3) a sensing surface adjacent to the first region, that molecules of the at least one type adhere to when the sensing surface is exposed to the molecules, the conductivity of the conducting channel being measurably affected by a local concentration of the adhering molecules near the position of the conducting channel; and
   b) a controller that controls power supplies to successively apply different voltages to the lateral gate electrodes of the transistor, moving the conducting channel to a plurality of different positions in a lateral direction, and at each position uses a circuit to measure the conductivity of the conducting channel by measuring a source to drain current at a source to drain voltage, and uses the measured conductivity to calculate a local concentration of the adhering molecules at that position.

2. A system according to claim 1, wherein the sensing surface is coated with a ligand that binds specifically to the molecules that are being sensed.

3. A system according to claim 1, wherein the source region and drain region are doped with dopants of a same sign, and the left and right lateral regions are doped with dopants of an opposite sign to the source and drain regions.

4. A system according to claim 3, wherein the first region is doped with a dopant of the same sign as the source and drain regions.

5. A system according to claim 4, wherein the concentration of dopants of the lateral regions extends into the first region, falling off gradually over a scale length greater than the width of the conducting channel.

6. A product manufactured by a process comprising:
   a) providing the system of claim 4; and
   b) heat treating the field effect transistor under conditions such that some of the dopants from the left and right lateral regions diffuse into the first region, reducing an effective width of the first region by at least 30% at its narrowest point, but not reducing the effective width to zero at any point.

7. A system according to claim 1, wherein the first region is narrower than 1 micrometer between the left and right lateral regions.

8. A system according to claim 1, wherein the field effect transistor also comprises a back gate electrode, located in a direction away from the sensing surface and separated from the first region at least by an insulator layer.

9. A system according to claim 1, which, for at least one choice of gate electrode voltages, would have a width of the conducting channel and a distance of the conducting channel from the sensing surface such that an equilibrium concentration of the adhering molecules could be determined when a concentration of the molecules in air that the sensing surface is exposed to is only 100 parts per million.

10. A system according to claim 1, wherein the at least one field effect transistor comprises a plurality of field effect transistors, with their sensing surfaces chemically modified in substantially a same way for binding to molecules in a gas or liquid sample, and the controller controls power supplies to change the lateral gate voltages to change the position of the conductive channel in a lateral direction in each transistor, and uses a circuit to measure the conductivity of the conductive channel at a plurality of different positions in each transistor, after exposing the sensing surfaces of the transistors to the sample, and calculates a greatest concentration of said molecules adhering near any of the positions, for each transistor, from the measured conductivities, and calculates an average over the transistors of the greatest concentrations of the adhering molecules.

11. A system according to claim 1 for use as an electronic nose for sensing a plurality of different types of molecules, wherein the at least one field effect transistor comprises a plurality of field effect transistors with sensing surfaces having different chemical properties, causing them to have different relative tendencies for the different molecules to adhere to them, and the controller controls power supplies to change lateral gate voltages to change the position of the conducting channel in a lateral direction, and calculates a concentration of any adhering molecules near each of the positions of the conducting channels after the sensing surfaces are exposed to a gas or liquid sample, from the conductivity measured at each of the positions, for each transistor, and finds the type of molecules present in the sample by comparing a pattern of the concentrations of molecules adhering to each field effect transistor, to an expected pattern of concentrations of adhering molecules for each of the types of molecules.

12. A system according to claim 1, wherein the field effect transistor also comprises a dielectric layer situated over the first region, wherein the sensing surface comprises a surface of the dielectric layer.

13. A system according to claim 1, wherein the sensing surface of the transistor comprises an exposed surface of the first region.

14. A system according to claim 13, wherein the semiconductor comprises silicon, and the exposed surface of the active region comprises methyl-terminated silicon.

15. A system according to claim 1, wherein the sensing surface lacks a reservoir for holding a liquid sample.

16. A system according to claim 1, also comprising a reservoir that includes the sensing surface, exposing the sensing surface to liquid samples contained in the reservoir.

17. A system according to claim 1, wherein the controller measures the source to drain current at a source to drain voltage by one or more of keeping the voltage at a constant value at the different positions and measuring changes in the current, keeping the current at a constant value at the different positions and measuring changes in the voltage, and keeping a function of the current and the voltage at a constant value at the different positions and measuring changes in a different function of the current and the voltage.

18. A method of modifying a multi-gate field effect transistor usable for sensing at least one type of molecules in a gas or liquid sample and comprising:
   a) a piece of semiconductor with a first region extending between a source region and a drain region, and left and right lateral regions extending along the first region on different sides, the source region and drain region doped with dopants of a same sign, the left and right lateral regions doped with dopants of an opposite sign to the source and drain regions, and the first region doped with a dopant of the same sign as the source and drain regions;
   b) left and right lateral gate electrodes that respectively produce an electric field in the left and right lateral regions, creating a conducting channel in the first region when appropriate voltages are applied to them, a position of the conducting channel depending on the applied voltages; and
   c) a sensing surface adjacent to the first region, that molecules of the at least one type adhere to when the sensing surface is exposed to the molecules, the conductivity of the conducting channel being measurably affected by a local concentration of the adhering molecules near the position of the conducting channel;
the method comprising heat treating the transistor under conditions such that some of the dopants from the left and right lateral regions diffuse into the first region, reducing an effective width of the first region by at least 30% at its narrowest point, but not reducing the effective width to zero at any point.

* * * * *